(12) United States Patent
Tonmukayakul et al.

(10) Patent No.: US 8,024,962 B2
(45) Date of Patent: Sep. 27, 2011

(54) FLOW-THROUGH APPARATUS FOR TESTING PARTICLE LADEN FLUIDS AND METHODS OF MAKING AND USING SAME

(75) Inventors: Narongsak Tonmukayakul, Duncan, OK (US); Jeff Morris, Riverdale, NY (US); Jason Bryant, Duncan, OK (US); Malcolm Talbot, Duncan, OK (US); Roger Schultz, Aubrey, TX (US); Robert Pipkin, Marlow, OK (US)

(73) Assignee: Halliburton Energy Services Inc., Duncan, OK (US)

( * ) Notice: Subject to any disclaimer, the term of this patent is extended or adjusted under 35 U.S.C. 154(b) by 398 days.

(21) Appl. No.: 12/180,668

(22) Filed: Jul. 28, 2008

(65) Prior Publication Data

US 2010/0018294 A1    Jan. 28, 2010

(51) Int. Cl.
   *G01N 11/14* (2006.01)
(52) U.S. Cl. .................. 73/54.28; 73/61.68
(58) Field of Classification Search .......... 73/54.28
   See application file for complete search history.

(56) References Cited

U.S. PATENT DOCUMENTS

| | | | |
|---|---|---|---|
| 2,626,786 A | 1/1953 | McGlothlin | |
| 2,846,873 A * | 8/1958 | Kalle | 73/54.28 |
| 3,269,171 A | 8/1966 | Bruss et al. | |
| 4,283,938 A | 8/1981 | Epper et al. | |
| 4,468,953 A | 9/1984 | Garritano | |
| 4,524,611 A | 6/1985 | Richon et al. | |
| 4,557,142 A | 12/1985 | Hensley et al. | |
| 4,612,800 A | 9/1986 | Erian | |
| 4,653,313 A | 3/1987 | Sabins et al. | |
| 4,829,811 A | 5/1989 | Ehlert et al. | |
| 5,042,292 A * | 8/1991 | Plint et al. | 73/54.28 |
| 5,708,197 A * | 1/1998 | Todd et al. | 73/54.28 |
| 5,799,734 A | 9/1998 | Norman et al. | |

(Continued)

FOREIGN PATENT DOCUMENTS

EP    0399634 A2    11/1990

(Continued)

OTHER PUBLICATIONS

Lord, D. L., "Helical screw rheometer: a new tool for stimulation," SPE 18213, 63rd Annual Technical Conference and Exhibition of the Society of Petroleum Engineers, Houston, Texas, Oct. 2-5, 1988, 7 pages, Society of Petroleum Engineers.

(Continued)

*Primary Examiner* — Hezron E Williams
*Assistant Examiner* — Paul West
(74) *Attorney, Agent, or Firm* — John W. Wustenberg; Conley Rose, P.C.

(57) ABSTRACT

A method of determining one or more bulk rheological properties of a particle laden fluid comprising providing a system comprising a vessel, a pump coupled to the vessel, and a flow-through apparatus coupled to the pump and the vessel, wherein the flow-through apparatus comprises a flow chamber, a bob rotatably disposed within the chamber, wherein the bob comprises an outer geometry adapted for continuous laminar flow in an axial direction, and a gap between the chamber and the bob, pumping the particle laden fluid into the flow-through apparatus, shearing the particle laden fluid within the gap of the flow-through apparatus, and collecting data from the bob and observing the particle laden fluid to determine one or more bulk rheological properties of the particle laden fluid.

20 Claims, 18 Drawing Sheets

U.S. PATENT DOCUMENTS

| | | | |
|---|---|---|---|
| 6,055,874 A * | 5/2000 | Onan et al. | 73/865.6 |
| 6,257,051 B1 | 7/2001 | Boyle et al. | |
| 6,584,833 B1 * | 7/2003 | Jamison et al. | 73/61.63 |
| 6,629,451 B1 | 10/2003 | Taylor | |
| 6,708,554 B2 | 3/2004 | Hettwer et al. | |
| 6,755,079 B1 | 6/2004 | Proett et al. | |
| 6,782,735 B2 | 8/2004 | Walters et al. | |
| 6,874,353 B2 | 4/2005 | Johnson et al. | |
| 6,997,045 B2 | 2/2006 | Wallevik et al. | |
| 7,079,244 B2 | 7/2006 | Gold et al. | |
| 7,392,842 B2 | 7/2008 | Morgan et al. | |
| 7,568,380 B2 | 8/2009 | Bivens et al. | |
| 7,712,526 B2 * | 5/2010 | Morgan et al. | 166/250.1 |
| 2004/0126874 A1 | 7/2004 | Sakai et al. | |
| 2008/0047328 A1 * | 2/2008 | Wang | 73/54.39 |
| 2008/0062212 A1 | 3/2008 | Na | |

FOREIGN PATENT DOCUMENTS

| | | |
|---|---|---|
| EP | 1712890 A2 | 10/2006 |
| GB | 2188162 A | 9/1987 |

OTHER PUBLICATIONS

Lord, D. L., et al., "Real-time fracturing fluid rheology measurements with the helical screw rheometer," SPE 19734, 64th Annual Technical Conference and Exhibition of the Society of Petroleum Engineers, San Antonio, Texas, Oct. 8-11, 1989, 8 pages, Society of Petroleum Engineers.

Nakken, Torgeir, et al., "Measurements of polymer induced drag reduction and polymer scission in Taylor flow using standard double-gap sample holders with axial symmetry," Journal of Non-Newtonian Fluid Mechanics, 2001, pp. 1-12, Elsevier Science B.V.

Patent application entitled "Device and method for testing friction reduction efficiency and suspension systems," by Narongsak Tonmukayakul, et al., filed Jul. 2, 2008 as U.S. Appl. No. 12/166,992.

Thesing, A., "New device for rheology measurements of proppant-laden fluids with the Fann 50 viscometer," SPE 58759, SPE International Symposium on Formation Damage Control, Lafayette, Louisiana, Feb. 23-24, 2000, pp. 1-10, Society of Petroleum Engineers.

Ancey, Christophe, "Solving the Couette inverse problem using a wavelet-vaguelette decompositon," J. Rheol., Mar./Apr. 2005, pp. 441-460, vol. 49, No. 2, The Society of Rheology, Inc.

Bird, R. Byron, et al., "Transport phenomena," Second Edition, Jul. 2001, 1 cover page and 1 figure, John Wiley & Sons Inc.

Brady, John F., et al., "Microstructure of strongly sheared suspensions and its impact on rheology and diffusion," J. Fluid Mech., 1997, pp. 103-139, vol. 348, Cambridge University Press, United Kingdom.

Clarke, B., "Rheology of coarse settling suspensions," 1967, pp. T251 to T256, vol. 45, Trans. Instn Chem. Engrs.

Krieger, Irvin M., "Rheology of monodisperse latices," Advances in Colloid and Interface Science, 1972, pp. 111-136, vol. 3, Elsevier Publishing Company, The Netherlands.

Morris, J. F., et al., "Pressure-driven flow of a suspension: buoyancy effects," Int. J. Multiphase Flow, 1998, pp. 105-130, vol. 24, No. 1, Elsevier Science Ltd., Great Britain.

Morris, Jeffrey F., et al., "Curvilinear flows of noncolloidal suspensions: the role of normal stresses,"J. Rheol., Sep./Oct. 1999, pp. 1213-1237, vol. 43, No. 5, The Society of Rheology, Inc.

Nguyen, Q. D., et al., "Characterization of yield stress fluids with concentric cylinder viscometers," 1987, pp. 508-515, vol. 26, No. 6, Rheologica Acta.

Nguyen, Q. D., et al., "Measuring the flow properties of yield stress fluids," Annu. Rev. Fluid Mech., 1992, pp. 47-88, vol. 24, Annual Reviews Inc.

Saraf, D. N., et al., "Some studies on the viscosity of settling suspensions," Aug. 1975, pp. 449-452, vol. 53, The Canadian Journal of Chemical Engineering.

Sparrow, E. M., et al., "Instability of the flow between rotating cylinders: the wide-gap problem," 1964, pp. 35-46, vol. 20, Part 1, J. Fluid Mech., Great Britain.

Stickel, Jonathan J., et al., "Fluid mechanics and rheology of dense suspensions," Annu. Rev. Fluid Mech., 2005, pp. 129-149, vol. 37, Annual Reviews.

Yeow, Y. Leong, "Solving the inverse problem of Couette viscometry by Tikhonov regularization," J. Rheol., Nov./Dec. 2000, pp. 1335-1351, vol. 44, No. 6, The Society of Rheology, Inc.

Foreign communication from a related counterpart application—International Search Report and Written Opinion, PCT/ GB2009/001654, Sep. 18, 2009, 12 pages.

Office Action dated Dec. 23, 2010 (21 pages), U.S. Appl. No. 12/166,992, filed Jul. 2, 2008.

Foreign communication from a related counterpart application—International Preliminary Report on Patentability, PCT/GB2009/001654, Feb. 1, 2011, 8 pages.

Final Office Action dated Apr. 18, 2011 (15 pages), U.S. Appl. No. 12/166,992, filed Jul. 2, 2008.

Notice of Allownace dated May 24, 2011 (7 pages), U.S. Appl. No. 12/166,992, filed on Jul. 2, 2008.

* cited by examiner

FLOW-THROUGH APPARATUS FOR TESTING PARTICLE LADEN FLUIDS AND METHODS OF MAKING AND USING SAME

CROSS-REFERENCE TO RELATED APPLICATIONS

The subject matter of the present application is related to U.S. patent application Ser. No. 12/166,992 filed Jul. 2, 2008 and entitled "Device and Method for Testing Friction Reduction Efficiency and Suspension Systems" and U.S. patent application Ser. No. 11/246,816 filed Oct. 7, 2005, now U.S. Pat. No. 7,392,842, and entitled "Proppant Suspension Testing Devices and Methods of Use," each of which is hereby incorporated herein by reference in its entirety for all purposes.

STATEMENT REGARDING FEDERALLY SPONSORED RESEARCH OR DEVELOPMENT

Not applicable.

REFERENCE TO A MICROFICHE APPENDIX

Not applicable.

BACKGROUND

1. Technical Field

The present disclosure generally relates to the field of rheometry. More specifically, this disclosure relates to a flow-through apparatus for testing particle laden fluids and methods of making and using same.

2. Background

Various industries such as the oil industry may need to test particle laden fluids or systems to determine if they are suitable for their intended use. However, in particle laden fluids or suspensions, the particulate matter has a tendency to settle during an experiment and thus, an inaccurate measurement may result. Conventional rheometers do not take into account this settling effect in particle laden fluids nor do they maintain particle laden fluids in suspension. Accordingly, reliable testing of the effect of particle settling on the particle laden fluid has been problematic due to the fact that existing rheometers have been unable to measure to a desired accuracy the rheological properties such as viscosity in a fluid having a high concentration of solids or particles. Consequently, there is a need for improved methods and devices for suspension testing of particle laden fluids.

SUMMARY

Disclosed herein is a method of determining one or more bulk rheological properties of a particle laden fluid comprising (a) providing a system comprising a vessel, a pump coupled to the vessel, and a flow-through apparatus coupled to the pump and the vessel, wherein the flow-through apparatus comprises a flow chamber, a bob rotatably disposed within the chamber, wherein the bob comprises an outer geometry adapted for continuous laminar flow in an axial direction, and a gap between the chamber and the bob, (b) pumping the particle laden fluid into the flow-through apparatus, (c) shearing the particle laden fluid within the gap of the flow-through apparatus, and (d) collecting data from the bob and observing the particle laden fluid to determine one or more bulk rheological properties of the particle laden fluid. The method may comprise shearing the fluid within the gap as the bob rotates and the fluid continuously flows through the flow chamber of the flow-through apparatus. The method may comprise shearing the fluid within the gap as the bob remains stationary and the fluid continuously flows through the flow chamber. The method may comprise shearing the fluid within the gap by rotating the bob while the fluid remains stationary within flow chamber. The method may comprise shearing the fluid within the gap as the bob and the fluid remains stationary within flow chamber. The one or more bulk rheological properties may comprise shear stress, viscosity, fluid velocity, or combinations thereof. The method may further comprise heating the particle laden fluid within the vessel. The method may further comprise measuring the pressure from the top to the bottom of the vessel, from the top to the bottom of the flow-through apparatus, or combinations thereof. The method may further comprise measuring the temperature of the fluid at one or more locations within the system. The one or more locations may comprise inside the vessel, inside the sample conditioning unit, inside the flow-through apparatus, or combinations thereof. The method may further comprise changing the rotational speed of the bob and repeating (c) and (d). The method may further comprise changing the size of the bob. The method may further comprise changing the speed of the pump. The flow chamber further may comprise a view portion. The method may further comprise visually or optically observing the particle laden fluid within the flow-through device through the view portion. The method may further comprise pre-conditioning the particle laden fluid before (b) to simulate downhole conditions. The particle laden fluid may be a fracturing fluid. The particle laden fluid may be a fluid to be used in a wellbore servicing.

Also disclosed herein is a system for testing a particle laden fluid comprising a mixing vessel, a conditioning unit coupled to said mixing vessel for pre-conditioning the shear and the temperature of the particle laden fluid, a flow-through apparatus coupled to said conditioning unit and said mixing vessel, wherein said flow-through apparatus comprises a flow chamber having a view portion, one or more inlet and one or more outlet in fluid communication with said flow chamber, said inlet and said outlet allow for continuous flow of the particle laden fluid through said flow-through apparatus, and a bob rotatably disposed within said flow chamber, wherein said bob comprises an outer geometry adapted for continuous laminar flow in an axial direction, and wherein said view portion allows for optical and visual measurement of the particle laden fluid as said bob rotates and the particle laden fluid flows through said flow chamber.

The view portion may be transparent or translucent. The inlet may be positioned to allow the particle laden fluid to develop a laminar flow. The flow chamber may have an inner geometry substantially similar to the outer geometry of said bob. The flow-through apparatus may further comprise a gap between said flow chamber and said bob. The gap may comprise a distance sufficient to produce laminar flow. The bob may comprise a bob casing having an upper portion and a lower portion, a top bob element rotatably disposed within the upper portion of said casing, a bob connector rotatably coupled to the bottom of said top bob element, a bottom bob element coupled to the bottom of said connector within the lower position of said casing, a lower shaft coupled to said bottom bob element, and an upper shaft coupled to said top bob element. The bottom bob element may be fixedly coupled to said lower shaft. The upper portion and the lower portion of bob casing may be frusto-conical. The connector may comprise ball bearings, ultra precision ball bearings, or combinations thereof. The flow-through apparatus may further comprise one or more sensors disposed within said flow-through apparatus. The sensors may comprise pressure sensor, temperature sensor, flowrate sensor, viscosity sensor, torque sensor, or combinations thereof. The mixing vessel may comprise an impeller. The mixing vessel may comprise one or more pressure sensors. The mixing vessel may further comprise temperature sensors disposed within said mixing vessel. The mixing vessel may further comprise a heating or cooling element disposed interior or exterior to said mixing vessel. The system may further comprise a pump coupled to the mixing vessel and the sample conditioning unit. The sample conditioning unit may further comprise a plurality of sensors disposed within said sample conditioning unit. The plurality of sensors may comprise pressure sensors, temperature sensors, flow rate sensors, viscosity sensors, or combinations thereof. The system may further comprise one or more sample conditioning unit coupled to said flow-through apparatus and said mixing vessel for post-conditioning the particle laden fluid. The system may further comprise a computer system coupled to said mixing vessel, said pump, said sample conditioning unit, and said flow-through apparatus.

Further disclosed herein is an apparatus for testing a particle laden system comprising a flow chamber, wherein said flow chamber has a view portion. at least one inlet and at least one outlet in fluid communication with said flow chamber, said inlet and said outlet allow for continuous flow of the particle laden fluid through said flow-through apparatus, and a bob rotatably disposed within said flow chamber, wherein said bob comprises an outer geometry adapted for continuous laminar flow in an axial direction, and wherein said view portion allows for optical measurement and visual observation of the particle laden system as said bob rotates.

The view portion may be transparent or translucent. The view portion may be made from materials comprising glass, thermoplastic, polycarbonates, polymethylmethacrylate, stainless steel, or combinations thereof. The bob may comprise a bob casing having an upper portion and a lower portion, a top bob element rotatably disposed within said upper portion of said casing, a bob connector rotatably coupled to the bottom of said top bob element, a bottom bob element coupled to the bottom of said connector within said lower position in said casing; a lower shaft coupled to said bottom bob element, and an upper shaft coupled to said top bob element. The upper portion and the lower portion of bob casing may be frusto-conical.

BRIEF DESCRIPTION OF THE DRAWINGS

For a more complete understanding of the present disclosure and the advantages thereof, reference is now made to the following brief description, taken in connection with the accompanying drawings and detailed description.

NOTATION AND NOMENCLATURE

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ". Also, the term "couple" or "couples" is intended to mean either an indirect or direct connection. Thus, if a first device couples to a second device, that connection may be through a direct connection, or through an indirect connection via other devices and connections.

DETAILED DESCRIPTION

It should be understood at the outset that although an illustrative implementation of one or more embodiments is provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

Disclosed herein are systems and methods for testing particle laden fluids used in wellbore or downhole applications. The systems and methods may utilize a flow-through apparatus having a novel rotatable bob. The flow-through apparatus has a novel configuration which allows a fluid sample to continuously flow through a flow chamber in the axial direction while simultaneously shearing the fluid sample in the radial direction (perpendicular to the flow). In addition, the flow-through apparatus may have a view portion for real time visualization of particle settling in the fluid sample. Embodiments of the system also may include at least one mixing vessel, at least one pump, and at least one computer system, each of which will be described later herein. In some embodiments, the system may further include at least one sample conditioning unit. As used herein, the term "rheometer"

encompasses both multiple-speed testing and single-speed testing devices (the latter conventionally being referred to as a "viscometer" even if performed by the identical instrument capable of multiple-speed testing) for obtaining rheological properties of fluids.

The flow-through apparatus simulates downhole conditions and measures bulk rheological properties of particle laden fluids to provide information (e.g., bulk rheology properties) by measuring the fluid or mixture properties while the rotatable bob rotates. The disclosed methods and systems may also offer capability for a user to improve overall wellbore servicing performance based on such information.

Figure 1:
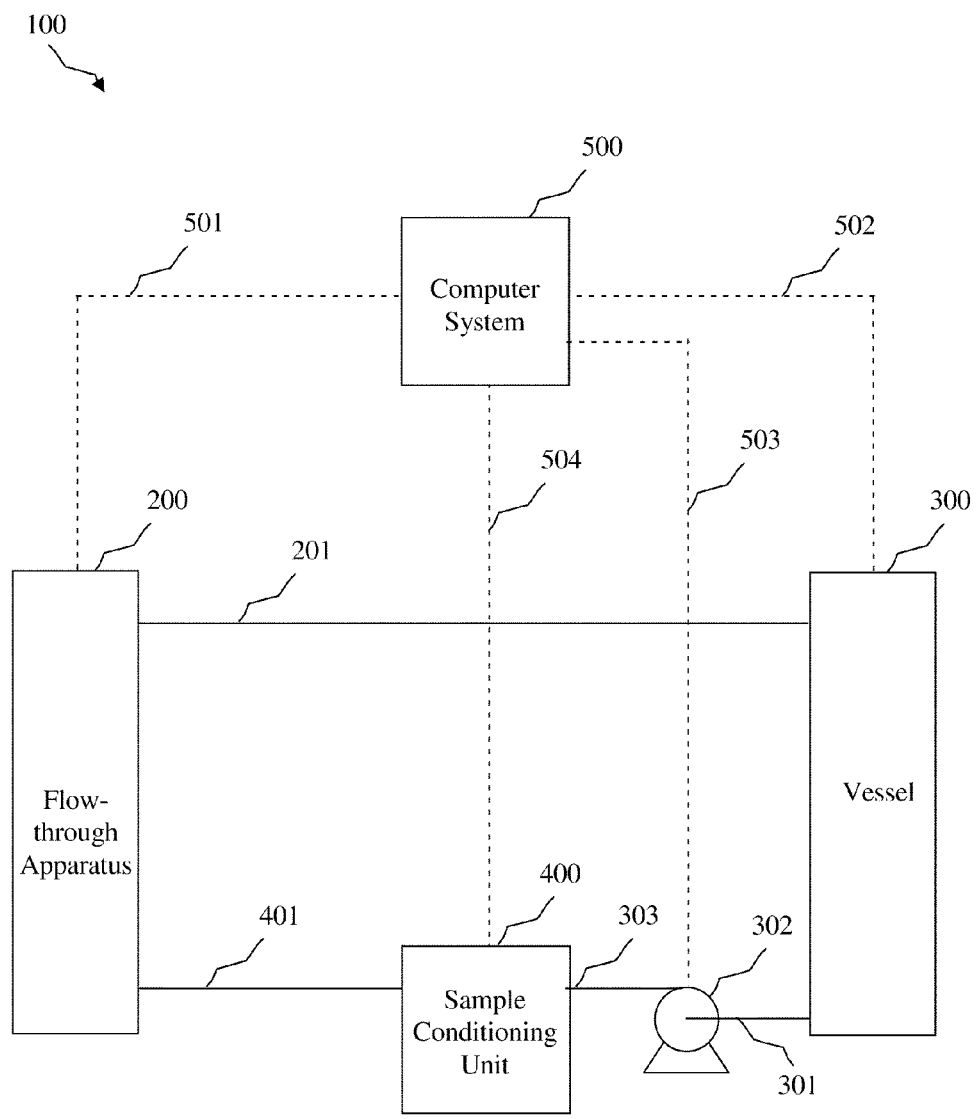
FIG. 1 illustrates a schematic view of an embodiment of components associated with a system for testing particle laden fluids.

FIG. 1 illustrates a schematic view of an embodiment of components associated with a system 100 for testing particle laden fluids. Generally, these components may comprise a flow-through apparatus 200, a mixing vessel 300, a pump 302, and a computer system 500. The system 100 may further comprise one or more sample conditioning units 400. The apparatus 200 may be coupled to the mixing vessel 300 via flowline 201. The mixing vessel 300 may be coupled to the pump 302 via flowline 301, which in turn may be coupled to the sample conditioning unit 400 via flowline 303, which in turn may be coupled to the apparatus 200 via flowline 401. The apparatus 200, the mixing vessel 300, the pump 302, and the sample conditioning unit 400 may be all coupled to the computer system 500 via flowlines 501, 502, 503, and 504 respectively.

Figure 2:
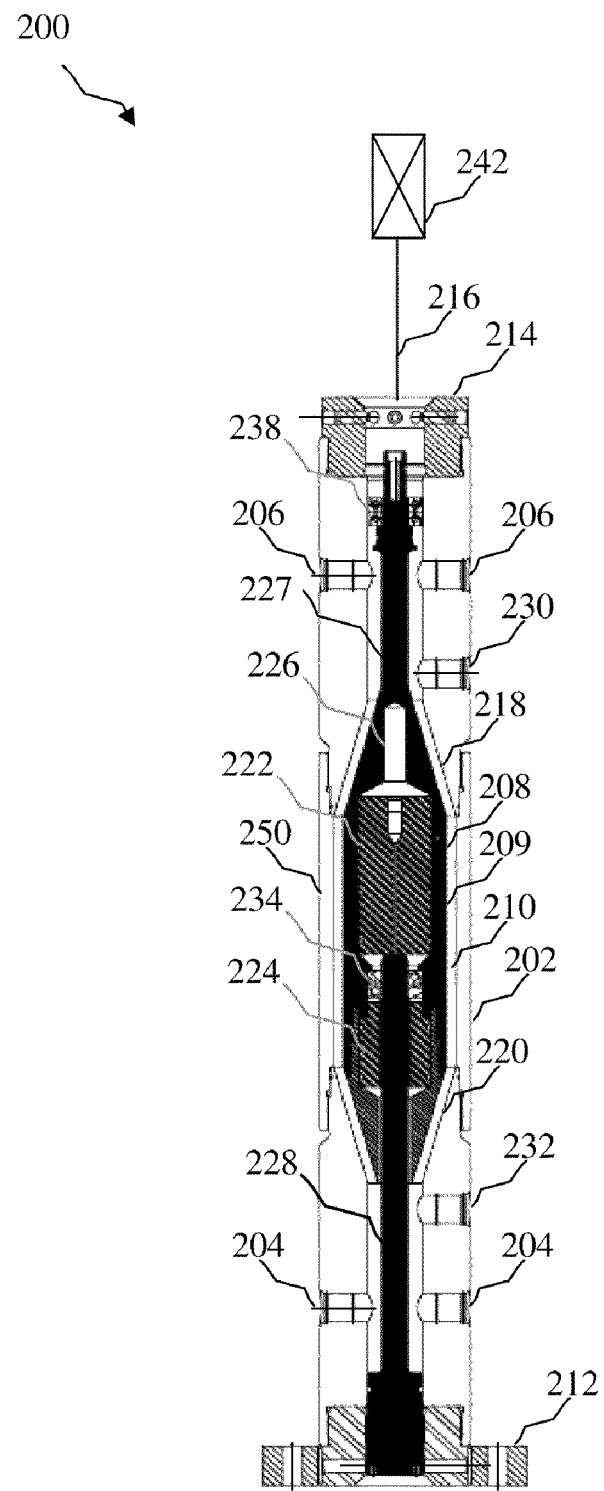
FIG. 2 illustrates a cross-sectional schematic of an embodiment of a mixing vessel.
Figure 3:
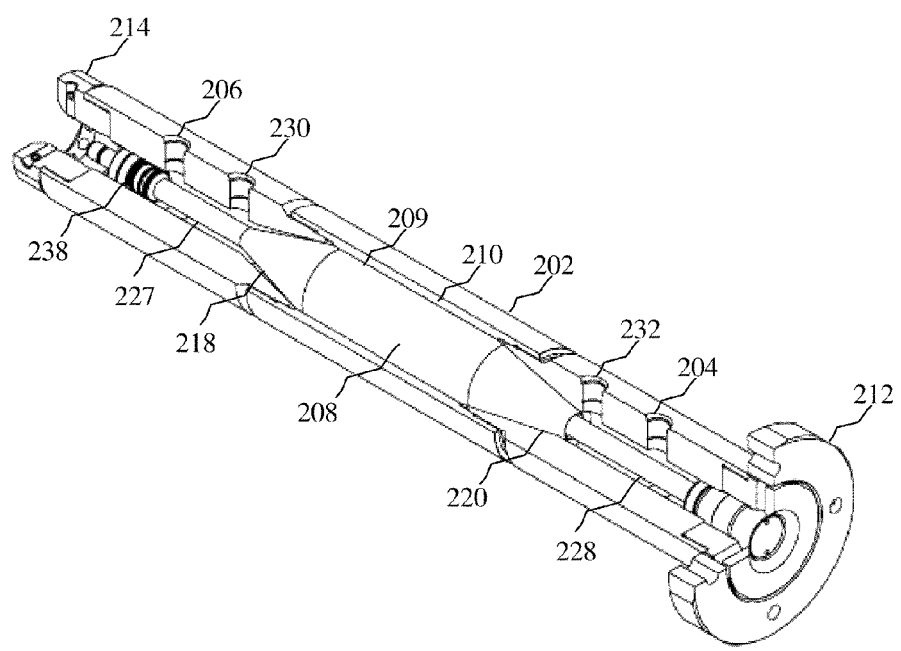
FIG. 3 illustrates a cross-sectional schematic of an embodiment of a flow-through apparatus.

FIG. 2 illustrates a cross-sectional schematic of an embodiment of a flow-through apparatus and FIG. 3 illustrates a perspective view of an embodiment of a flow-through apparatus.

Referring to FIG. 2, the flow-through apparatus 200 generally includes a flow chamber 202, a bottom cap 212 located at the bottom of the flow chamber 202, a top cap 214 located at the top of the flow chamber 202, and a bob 208 rotatably disposed within the flow chamber 202. As mentioned above, flow-through apparatus 200 has a novel configuration which allows for measurement of a particle laden fluid as it flows through flow chamber 202 as bob 208 shears the fluid in a radial direction.

In an embodiment, the flow chamber 202 is cylindrical in inner geometry. That is, inner radius of flow chamber 202 may be uniform over the length of flow chamber. However, flow chamber 202 may be configured with any suitable geometry. In another embodiment, flow chamber 202 may have an inner surface suitable to fit the bob 208 which will be further described below. In other words, radius of flow chamber 202 may be variable over the length of flow chamber 202. In an embodiment, the flow chamber 202 may have a ratio or radius to length of from about 0.2 to about 1, alternatively from about 0.2 to about 0.8, alternatively from about 0.2 to about 0.7. The bottom cap 212 and the top cap 214 may be configured in such a way (e.g., with set screws, with one or more seals, etc.) as to prevent fluid leakage. According to one embodiment, flow chamber 202 has at least one inlet 204 located at the lower portion of the flow chamber 202 and at least one outlet 206 located at the upper portion of the flow chamber 202. As shown in FIG. 2, there are two inlets 204 and two outlets 206. Inlet 204 and outlet 206 are in fluid communication with flow chamber 202. The locations of inlet 204 and outlet 206 may also be switched. That is, inlet 204 may be located at the upper portion of flow chamber 202 and outlet 206 may be located at lower portion of flow chamber 202. The location of the inlet 204 and the outlet 206 may be selected by one of ordinary skill in the art with the aid of this disclosure in such a way that stable laminar flow may be developed. For example, the location of the inlet 204 may be determined by the Entrance Length, which is defined in Equation 1 below:

$$EntranceLength = \frac{ELF \times v_z (R_o - \kappa R_o)^2 \rho}{\mu} \quad \text{Equation 1}$$

wherein ELF is effective length flow, $v_z$ is the axial flow velocity, $R_o$ is the outer radius of the bob 208, $\kappa$ is the gap ratio ($\kappa = R_i/R_o$), $R_i$ is the inner radius of the flow chamber 202, $\rho$ is the density of the fluid, and $\mu$ is the viscosity of the fluid. Further discussion on the entrance length may be found in Sparrow, E. M., Munro, W. D., and Jansson, V. K., *J. Fluid Mech.*, pp. 20, 35-46 (1964) and Bird, R. B., Stewart, W. E., and Lightfoot, E. N., "*Transport Phenomena*", Second Edition, John Wiley and Sons, ISBN 0-471-41077-2 (2002), which are incorporated by reference herein in their entirety.

The dimensions of the flow-through apparatus 200 such as the radius of the flow chamber 202, the location of the inlet 204 and outlet 206, etc. may be designed to allow for the development of stable laminar flow within the flow-through apparatus 200. The development of stable laminar flow may be evaluated based on the axial flow instability and the rotational flow instability. The axial flow instability may be determined by the Reynolds number (Re), which is defined in Equation 2 below:

$$Re = \frac{2R_i(1-\kappa)\rho v_z}{\mu} \quad \text{Equation 2}$$

wherein $R_i$ is the inner radius of the flow chamber 202, $\kappa$ is the gap ratio ($\kappa = R_i/R_o$), $\rho$ is the density of the fluid, $v_z$ is the axial flow velocity, and $\mu$ is the viscosity of the fluid. The radial and angular flow instability may be determined by the critical Taylor number (Ta), which is defined in Equation 3 below for Newtonian fluid:

$$Ta = \frac{v_\theta R_i(1-\kappa)}{v} \sqrt{\frac{(1-\kappa)}{\kappa}} \quad \text{Equation 3}$$

wherein $v_\theta$ is the radial flow velocity which typically equals to $v$, $R_i$, $\kappa$, and $v_z$ are same as described previously herein.

The inlet 204 may be coupled to the flow-through apparatus 200 via flow line 401. The outlet 206 may be coupled to the mixing vessel 300 via flowline 201. Sample from the fluid conditioning unit 400 may flow into the flow-through apparatus 200 through inlet 204, through gap 210 formed between the inner surface of the flow chamber 202 and the outer surface of the bob 208, and then finally flow out of the flow-through apparatus 200 through outlet 206. In an embodiment, the gap 210 comprises a distance sufficient to produce laminar flow. For example, the gap 210 may have a width between the inner surface of the flow chamber 202 and the outer surface of the bob 208 ranging from about 2 mm to about 10 mm, alternatively from about 4 mm to about 10 mm, alternatively from about 6 mm to about 10 mm.

A plurality of sensors may be used to measure various properties at different areas of flow-through apparatus 200. The sensors may be used to measure pressure, temperature, torque, shear stress, electrical conductivity, pH, or combinations thereof. In an embodiment, a pressure sensor or transducer may be disposed adjacent to the top or upper portion of flow chamber 202, for example placed via top port 230. Another pressure sensor or transducer may be disposed adjacent to the bottom or lower portion of flow chamber 202, for example placed via bottom port 232. The pressure sensors or transducers may be used to determine pressure drop from the top to the bottom of flow chamber 202.

According to one embodiment, flow chamber 202 may have a view portion 250. View portion 250 may be a portion of flow chamber 206 defined from the bottom of bob 208 to the top of bob 208. In an embodiment, view portion 250 allows visual or optical measurement around the entire outer perimeter of flow chamber. In another embodiment, view portion 250 may allow observation of only portions (e.g. ½ view or ¼ view) of the flow chamber. In such embodiment, view portion 250 allows in situ visualization and measurement of particle settling of the particle laden fluid within flow chamber 202 as a sample flows through flow chamber 202. View portion 250 of flow chamber 202 may be constructed using a variety of materials that may be selected by one of ordinary skill in the art with the aid of this disclosure. Examples of suitable view portion 250 materials that are transparent include without limitation glass, thermoplastic such as polycarbonates, which is commercially available under the tradename LEXAN from SABIC Innovative Plastics (previously General Electric's Plastics), polymethylmethacrylate (PMMA), which is commercially available under the tradenames PLEXIGLAS®, LIMACRYL®, R-CAST®, PERSPEX®, PLAZCRYL®, ACRYLEX®, ACRYLITE®, ACRYPLAST®, ALTUGLAS®, POLYCAST®, or LUCITE®. Alternatively, the flow chamber 202 is constructed such as to allow light transmission, light scattering, or other optical devices for measuring properties of the test sample. Alternatively, the view portion 250 of the flow chamber 202 may be constructed from opaque materials such as without limitation, stainless steel, glass, thermoplastic, or combinations thereof.

Bob 208 is generally disposed within the interior hollow volume of flow chamber 202. Furthermore, the bob 208 may be coaxially or concentrically disposed within the interior hollow volume of flow chamber 202. The bob 208 may also be hollow to reduce weight and thus minimize friction.

In an embodiment, the bob 208 has an outer geometry suitable for developing laminar axial flow across its surface. As used herein, "laminar" flow may refer to smooth or non-turbulent flow. Fluid sample should be capable of flowing through flow chamber and over bob 208 in a laminar fashion. Accordingly, bob 208 may comprise an outer bob casing 209 having a top bob element 222 and a bottom bob element 224. Bob casing 209 encases bob elements 222, 224 to provide a uniform surface for laminar flow of fluid sample as fluid flows through flow chamber 202. Top bob element 222 may be disposed within the upper portion of bob casing 209. A bob connector 234 may be coupled to the bottom of the top bob element 222. Bottom bob element 224 may be coupled to the bottom of the bob connector 234 within the lower position in the bob casing 209. In addition, an upper shaft 227 may be coupled to the top bob element 222 and a lower shaft 228 may be connected to the bottom bob element 224.

In an embodiment, top bob element 222 is rotatably coupled to bob connector 234 while bottom bob element 224 is fixedly coupled to bob connector 234. In such an embodiment, upper shaft 227 is fixedly attached to the top bob element 222, and lower shaft 228 is fixedly attached to bottom bob element 224 and bottom cap 212. In this way, as top bob element 222 causes bob casing 209 to rotate and shear fluid, bottom bob element 224 remains stationary. Thus, bob connector 234 acts as a bearing for the rotation of top bob element 222.

The geometry of the bob casing 209 may be any suitable shape that provides laminar axial flow in flow chamber 202. In an embodiment, the geometry of bob casing 209 is adapted for continuous laminar flow in an axial direction. In such embodiment, the outer geometry of bob casing 209 may be substantially similar to the inner geometry of the flow chamber 202. For example, the bob casing 209 is cylindrical in its geometry having a radius of from about 30 millimeters (mm) to about 65 mm, alternatively from about 45 mm to about 65 mm, alternatively from about 50 mm to about 65 mm and a length of from about 100 mm to about 250 mm, alternatively from about 125 mm to about 200 mm, alternatively from about 150 mm to about 175 mm; and a ratio of outer radius of bob casing 209:inner radius of flow chamber 202 of from about 0.3 to about 0.9, alternatively from about 0.5 to about 0.95, alternatively from about 0.75 to about 0.98. In some embodiments, the bob casing 209 may further have a frusto-conical surface 218 at the top and an inverted frusto-conical surface 220 at the bottom so as to guide or channel flow of the test sample into gap 210. In other words, inlet 204 may be funnel-shaped to guide a fluid sample into gap 210 and inverted funnel-shaped to guide the fluid sample out of outlet 206.

As explained above, in certain embodiments, bob connector 234 may comprise ball-bearings, or alternatively ultra precision ball bearings. Generally, ball bearing connectors are used to minimize rotational friction. The ball bearings may be made from any suitable material such as stainless steel, ceramic hybrid (e.g., silicon nitride), and the like. However, bob connector 234 may be any other coupling which allows bob connector 234 to act as a bearing between top bob element 222 and bottom bob element 224.

The top bob element 222 may be fixedly disposed within the bob casing 209 which may be further coupled to a shaft 216 via a connector 238, which in turn may be coupled to a driver unit 242 (e.g., motor) for rotating bob 208 and its top bob element 222. Accordingly, bob 208 and its top bob element 222 rotates within flow chamber 202 via shaft 216 and driver unit 242. The connector 238 may be a connector type similar to the bob connector 234. The driver unit 242 may be any known means for rotating bob such as without limitation, engines, mixers, motors, etc. Furthermore, the driver unit 242 may incorporate a torque sensor for measuring the force of the sample exerted on bob 208. In some embodiments, bob 208, top bob element 222, and bottom bob element 224 may be removable from chamber 202 and interchangeable such that different sized, weight, and/or shaped bobs may be used to adjust the gap 210. The top bob element 222 may be configured in any shape or geometry. For example, the top bob element 222 may have a similar geometry to the bob casing 209.

The bottom bob element 224 may be used to fill the bob casing 209 and prevent leakage into the inside of the bob 208. The bottom bob element 224 may be coupled to a lower shaft 228. In an embodiment, the lower shaft 228 may be an alignment shaft that is fixedly coupled to the bottom cap 212 of the flow chamber 202 and the top bob element 222, as shown in FIG. 2, such as to align the bob 208 coaxially or concentrically in the center of the flow chamber 202. In such embodiment, the bottom bob element 224 may remain stationary, while the bob 208 and its top bob element 222 may rotate via shaft 216 and driver unit 242. The bottom bob element 224 may also be configured in any shape or geometry. In any case, the bob 208, the top bob element 222 and the bottom bob element 224 may further be removable from the interior volume of flow chamber 202 for disassembly, storage, transport, cleaning, etc.

Figure 4:
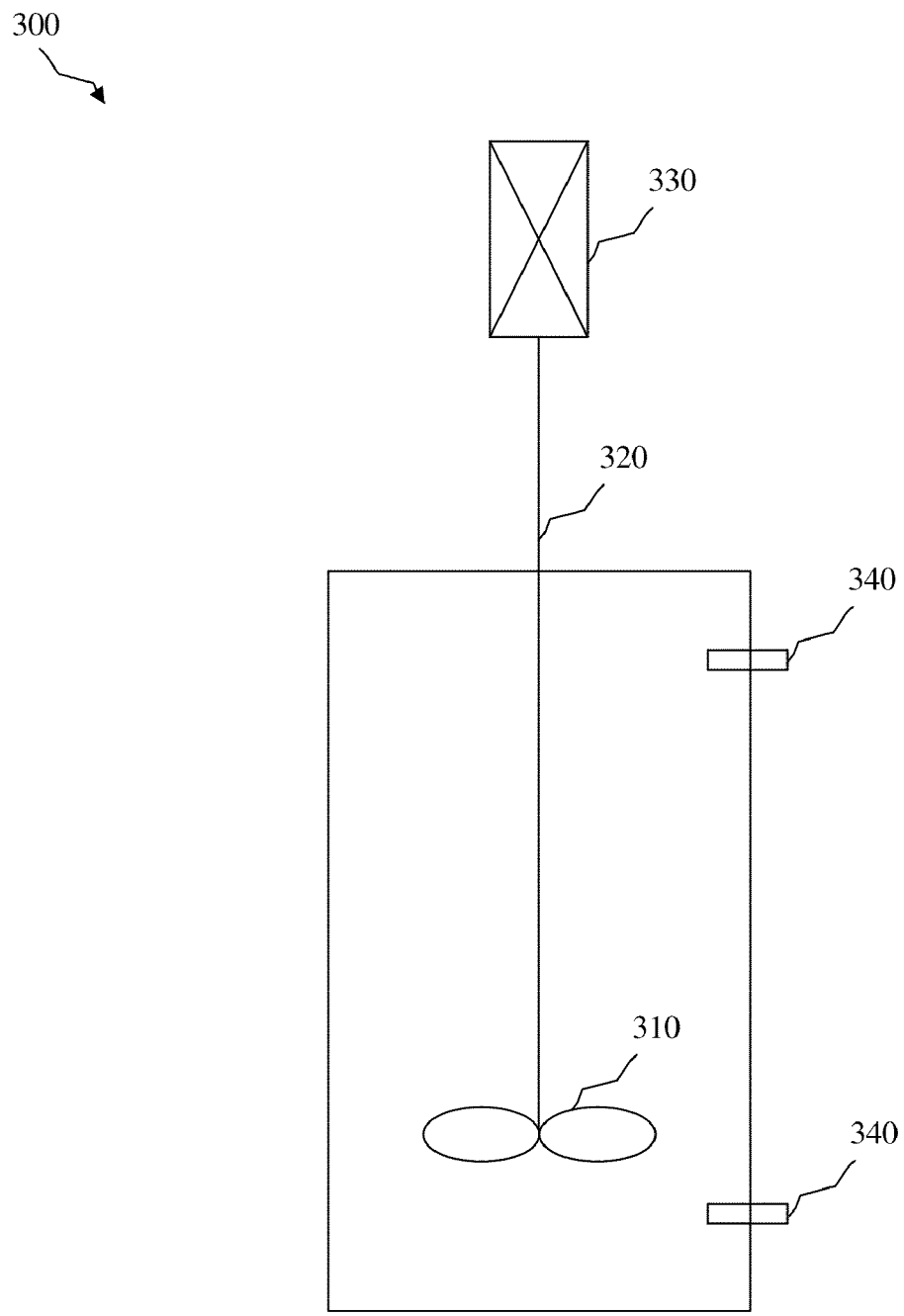
FIG. 4 illustrates a side view of an embodiment of a flow-through apparatus.

Referring back to FIG. 1, the flow-through apparatus 200 is coupled to the mixing vessel 300 via flowline 201. FIG. 4 illustrates a schematic of an embodiment of a mixing vessel 300. The mixing vessel 300 (or tank, container, unit, etc.) may be open or enclosed and may be constructed from any suitable material for example metal, composite, glass, plastics, etc. The mixing vessel 300 may be coupled to a mixer 310 (or an agitator) that mixes or agitates the components within the mixing vessel 300. The mixer 310 may be coupled to a shaft 320, which in turn may be coupled to a driver unit 330 (e.g., motor) for rotating the mixer 310. The driver unit 330 may be any known means for rotating mixer 310 such as without limitation, engines, mixers, motors, etc. In an embodiment, the mixing vessel 300 mixes the components at a desired treatment rate to achieve a well-blended mixture (e.g., fracturing fluid, cement slurry, liquefied inert gas, etc.).

Moreover, pressure sensors or transducers 340 may be placed adjacent the upper and lower portions of the mixing vessel 300 to determine pressure drop from the top to the bottom of the mixing vessel 300.

The mixing vessel 300 may be further equipped with a heating or cooling element to control the temperature of the particle laden fluid. For example, a heating or cooling coil and/or jacket may be disposed interior and/or exterior to the mixing vessel 300. Alternatively, the mixing vessel 300 may be immersed in a heating or cooling bath.

The mixing vessel 300 may be used to mix the fluid and solid components of the particle laden fluids which include without limitation proppants, water, chemicals, cement, cement additives, or combinations thereof. The mixing conditions including time period, agitation method, pressure, and temperature of the mixing vessel 300 may be chosen by one of ordinary skill in the art with the aid of this disclosure to produce a homogeneous blend of the desired composition, density, and viscosity or to otherwise meet user desired properties.

Referring back to FIG. 1, the mixing vessel 300 is coupled to the pump 302 via flowline 301. The pump 302 may include any suitable pump that can pressurize and control the flow of the particle laden fluid. Examples of suitable pumps include without limitation centrifugal pumps, positive displacement pumps, reciprocating pumps, high pressure pumps, and the like. The speed of the pump 302 may be increased or decreased to achieve a desirable flowrate of the particle laden fluid.

The pump 302 is coupled to the sample conditioning unit 400 via flowline 303. The sample conditioning unit 400 may be used to condition the particle laden fluid to user desired properties (e.g., temperature, pressure, viscosity, etc.) prior to entering the flow-through apparatus 200. Specifically, sample conditioning unit 400 is used to expose the particle laden fluid to simulated conditions in a downhole environment. A plurality of sensors may be used to measure various fluid properties such as pressure, temperature, flow rate, viscosity, electrical conductivity, pH, light transmission, or combinations thereof. For example, temperature sensors, which may be any devices known to those of skill in the art with the aid of this disclosure capable of measuring temperature such as thermocouples, thermometers, etc., may be disposed within the sample conditioning unit 400 such that one or more sensors are in contact with and/or measure the temperature of the particle laden fluid in the sample conditioning unit 400. Additionally, pressure sensors or transducers may be placed within the sample conditioning unit 400 to determine the pressure of the particle laden fluid prior to entering and/or leaving the flow-through apparatus 200. The sample conditioning unit 400 may be further equipped with a heater and/or cooler of the type described previously herein to control the temperature of the particle laden fluid.

If desired, another sample conditioning unit 400 (not shown in FIG. 1) may be coupled to the flow-through apparatus 200 and the mixing vessel 300. The additional sample conditioning unit 400 may be used for example to check the properties of fluid after it passes through the flow-through apparatus 200.

Figure 5:
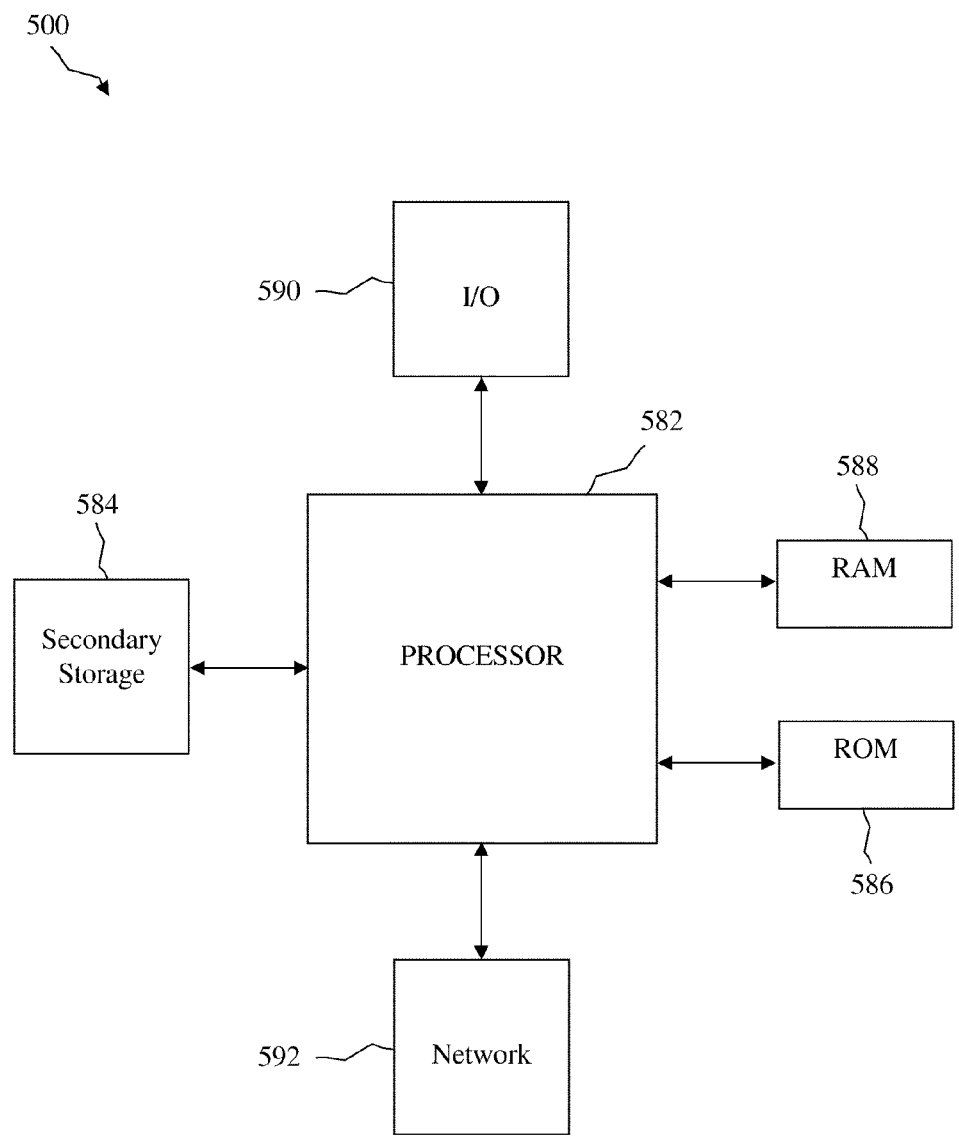
FIG. 5 illustrates an exemplary general purpose computer system suitable for implementing the several embodiments of the disclosure.

Referring back to FIG. 1, the apparatus 200, the mixing vessel 300, the pump 302, and the sample conditioning unit 400 may be all coupled to the computer system 500 via flowlines 501, 502, 503, and 504 respectively. The computer system 500 may be implemented on any general-purpose computer with sufficient processing power, memory resources, and network throughput capability to handle the necessary workload placed upon it. FIG. 5 illustrates a typical, general-purpose computer system 500 suitable for implementing one or more embodiments disclosed herein. The computer system 500 includes a processor 582 (which may be referred to as a central processor unit or CPU) that is in communication with memory devices including secondary storage 584, read only memory (ROM) 586, random access memory (RAM) 588, input/output (I/O) 590 devices, and network connectivity devices 592. The processor may be implemented as one or more CPU chips.

The secondary storage 584 is typically comprised of one or more disk drives or tape drives and is used for non-volatile storage of data and as an over-flow data storage device if RAM 588 is not large enough to hold all working data. Secondary storage 584 may be used to store programs which are loaded into RAM 588 when such programs are selected for execution. The ROM 586 is used to store instructions and perhaps data which are read during program execution. ROM 586 is a non-volatile memory device which typically has a small memory capacity relative to the larger memory capacity of secondary storage. The RAM 588 is used to store volatile data and perhaps to store instructions. Access to both ROM 586 and RAM 588 is typically faster than to secondary storage 584.

I/O 590 devices may include printers, video monitors, liquid crystal displays (LCDs), touch screen displays, keyboards, keypads, switches, dials, mice, track balls, voice recognizers, card readers, paper tape readers, or other well-known input and output devices. The network connectivity devices 592 may take the form of modems, modem banks, ethernet cards, universal serial bus (USB) interface cards, serial interfaces, token ring cards, fiber distributed data interface (FDDI) cards, wireless local area network (WLAN) cards, radio transceiver cards such as code division multiple access (CDMA) and/or global system for mobile communications (GSM) radio transceiver cards, and other well-known network devices. These network connectivity 592 devices may enable the processor 582 to communicate with an Internet or one or more intranets. With such a network connection, it is contemplated that the processor 582 might receive information from the network, or might output information to the network in the course of performing the above-described method steps. Such information, which is often represented as a sequence of instructions to be executed using processor 582, may be received from and outputted to the network, for example, in the form of a computer data signal embodied in a carrier wave.

Such information, which may include data or instructions to be executed using processor 582 for example, may be received from and outputted to the network, for example, in the form of a computer data baseband signal or signal embodied in a carrier wave. The baseband signal or signal embodied in the carrier wave generated by the network connectivity 592 devices may propagate in or on the surface of electrical conductors, in coaxial cables, in waveguides, in optical media, for example optical fiber, or in the air or free space. The information contained in the baseband signal or signal embedded in the carrier wave may be ordered according to different sequences, as may be desirable for either processing or generating the information or transmitting or receiving the information. The baseband signal or signal embedded in the carrier wave, or other types of signals currently used or hereafter developed, referred to herein as the transmission medium, may be generated according to several methods well known to one skilled in the art.

The processor 582 executes instructions, codes, computer programs, scripts which it accesses from hard disk, floppy disk, optical disk (these various disk based systems may all be considered secondary storage 584), ROM 586, RAM 588, or the network connectivity devices 592.

The computer system 500 may also comprise a communication unit 596 capable of facilitating communications between the processor 582 and the flow-through apparatus 200, the mixing vessel 300, and the sample conditioning unit 400. Alternatively, the communication unit 596 is capable of providing transmission and reception of electronic signals to and from an external communications unit. Alternatively, communication unit 596 may be a wireless device capable of transmitting and receiving signals to and from the flow-through apparatus 200, the mixing vessel 300, and the sample conditioning unit 400 without the use of wires, inter alia.

Sensors (e.g., pressure sensors or transducers 340, temperature sensors, flow rate sensors, viscosity sensors, etc.) may be coupled to the computer system 500 such that data obtained from sensors may be stored and/or used by the computer system 500. The computer system 500 is capable of receiving internal data and/or external data and generating and delivering signals to the flow-through apparatus 200, the mixing vessel 300, the pump 302, and the sample conditioning unit 400. For example, the computer system 500 may receive automated and/or manual instructions from a user input, and may send signals to the flow-through apparatus 200, the mixing vessel 300, the pump 302, and the sample conditioning unit 400 based on internal calculations, programming, and/or data received from sensors. Thus, computer system 500 may be coupled to driver unit 242 for rotating the bob 208 and/or driver unit 330 for rotating the shaft 320 and mixer 310. The computer system 500 may also be coupled to a heating or cooling element to control the temperature of the sample based upon feedback from the temperature samples. The computer system 500 may also be coupled to the pump 302 to control the flow of the particle laden fluid based upon feedback from any one or more of the pressure transducers of the system 100. As such, the computer system 500 may be capable of affecting various functions of the system 100, the flow-through apparatus 200, the mixing vessel 300, the pump 302, and the sample conditioning unit 400 such as driver unit (e.g., 330, 242) speed, bob 208 speed, temperature of sample, pressure within the mixing vessel 300, pressure within the flow-through apparatus 200, pump 302 speed, and the like. However, it is also envisioned in some embodiments, speed control of bob 208, mixer 310, and/or pump 302 may be adjusted manually by controller units external to the computer system 500.

In an embodiment, a method of measuring one or more bulk rheological properties of a particle laden fluid comprises preparing a sample by loading the sample (e.g., a particle laden fluid) into the mixing vessel 300. The mixer 310 may be rotated at any suitable velocity (i.e., rotational speed) by turning on and adjusting the speed of the driver unit 330 to obtain a homogeneous mixture of the sample. In an embodiment, the mixer is rotated at rotational speeds ranging from about 0 rpm to about 4000 rpm, alternatively from about 10 rpm to about 3000 rpm, alternatively from about 100 rpm to about 2000 rpm. The sample may be heated or cooled using any suitable heating or cooling element as described previously herein. The properties (e.g., temperature, pressure, composition, etc.) of the sample may be monitored using sensors as described previously herein. For example, a pressure differential between the top and the bottom of the mixing vessel 300 may be measured to monitor settling and/or floating of proppants that may exist in the sample.

The sample may be fed to the pump 302 and conditioned in the sample conditioning unit 400. The speed of the pump may be adjusted according to the needs of the process. In an embodiment, the speed of the pump may range from about 0 liters per minute (lpm) to about 10 lpm, alternatively from about 0.1 lpm to about 7 lpm, alternatively from about 1 lpm to about 5 lpm. The conditions of the sample (e.g., shear, temperature, pressure, etc.) may be adjusted in the sample conditioning unit 400 to reach user desired conditions. For example, the conditions of the sample may be adjusted to simulate downhole conditions such as those found in a fracture path, flow in surface equipment, flow down the wellbore, and the like.

Once the sample reaches one or more user desired conditions, the sample may be fed to the flow-through apparatus 200 via one or more inlets 204. Herein, the sample may be sheared within the gap 210 of the flow-through apparatus 200. According to one embodiment, the sample may be continuously flowed through gap 210 and out of the flow-through apparatus 200 via one or more outlets 206 back into the mixing vessel 300. Fluid sample enters flow chamber 202 through inlets 204 and passes across outer surfaces of lower shaft 228, bob casing 209, and upper shaft 227. Because lower shaft 228, bob casing 209, and upper shaft 227 may be disposed coaxially within flow chamber 202, they provide a continuous and uniform surface over which the fluid sample may flow. In addition, the novel configuration of bob 208 (e.g. the frusto-conical shape of bob casing 209) allows for laminar flow through the flow chamber 202 while bob 208 is rotating. Bob 208 may be rotated at any suitable rotational speed (i.e., revolutions per minute), which applies a stress to the sample in the gap 210. In an embodiment, the bob 208 may be rotated at rotational speeds ranging from about 0 rpm to about 100 rpm, alternatively from about 0 rpm to about 75 rpm, alternatively from about 0 rpm to about 40 rpm. The stress applied to the outer surface of the bob 208 creates a torque on the bob 208. If the stress is sufficient, the sample will flow in the rotational direction. Torque acting on the outer surface of bob 208 may be measured and recorded as a function of the rotating speed and shearing time. More specifically, torque from the bob 208 may be measured by a sensor (e.g., a torque sensor) coupled to bob 208 through shaft 216. For example, the rotational speed of the bob 208 may be increased and/or decreased and the torque response to the change of the rotational speed of the bob 208 may be monitored and recorded. Mathematical formulas can be used to transform the dimensions of the bob 208 and flow chamber 202, and the corresponding torque measured by the bob 208 into a set of shear stress and shear rate data. For example, the shear rate may be obtained from the rotation speed of the bob and the width of the annular flow gap between the bob 208 and outer cylinder, while the torque measured is related to the shear stress on the bob surface through a similar geometric relation which may be determined by one of ordinary skill in the art with the aid of this disclosure. If desired, the bob 208 may be changed to any suitable size, shape, weight, dimension, etc. to meet the need of the user desired process. A pressure differential between the top and the bottom of the flow-through device 200 may also be measured to monitor settling and/or floating of proppants in the sample.

Another advantageous feature of the disclosed apparatus and system is that the settling and/or floating behavior of the sample inside the flow-through apparatus 200 may be observed. For example, if a transparent material is used for the chamber, any settling of particles may be visually observed. Alternatively, the sample may be optically observed using any optical device that may or may not require a transparent chamber to observe the sample. In such embodiments, an appropriate material for the chamber may be selected by one of ordinary skill in the art with the aid of this disclosure.

The system 100 may be operated in various modes of operation. In an embodiment, the system 100 may be operated with the pump 302 turned on and the bob 208 rotating simultaneously, wherein the sample is sheared within the gap 210 as the bob 208 rotates and the sample continuously flows through the flow chamber 202 of the flow apparatus 200. Alternatively, the system 100 may be operated with the pump 302 turned on and the bob 208 stationary, wherein the sample is sheared within the gap 210 as the bob 208 remains stationary and the sample continuously flows through the flow chamber 202 of the flow apparatus 200. Alternatively, the system 100 may be operated with the pump 302 turned off and the bob 208 rotating, wherein the sample is sheared as the bob 208 rotates and the sample remains stationary, for example after a period of recirculation within the flow-through apparatus 200 the pump may be turned off. Alternatively, the system 100 may be operated with the pump 302 turned off and the bob 208 stationary. Operation with the bob rotating, with or without axial flow through the chamber, allows measurement of the torque and as described previously herein this provides shear stress as a function of shear rate data. Such data is valuable for determining the quality of a downhole fluid and for modeling calculations used to predict its performance in well stimulation techniques. For example, such data may be used in development of hydraulic fracturing operation simulation tools that are widely known in the industry. Alternatively, the results with or without rotation of the bob when the axial flow is stopped provide information on the settling characteristics of individual proppant particles and assemblies of these particles at various levels of loading (concentration in, for example, pounds proppant per gallon of the liquid under test). This information is valuable for judging the efficacy of a fluid in its function as a proppant transport vehicle. It is also valuable for providing data for fracture simulators mentioned above and widely known in the industry.

Embodiments of the disclosed device and methods may be used to measure several different rheological properties including without limitation, yield stress, viscosity, shear stress, fluid mechanical variables such as fluid velocity, settling speed, shear rate, bulk fluid mechanical phenomena such as Taylor-Couette, and other instabilities and proppant structuring phenomena as described infra. In addition, chemically or physically induced changes in the material which affect these behaviors including rate of gelation and/or crosslinking, or combinations thereof may be monitored by the various measurements described.

In an embodiment, the disclosed system 100 may be used to conduct dynamic settling experiments. Specifically, the system 200 may be used to monitor the settling behavior of proppant in a sample. The sample may be deposited into the mixing vessel 300, circulated from the mixing vessel 300 to the pump, to the sample conditioning unit 400, to the flow-through apparatus 200, and back to the mixing vessel 300 for multiple times until the sample reaches conditions desired by the user. By such operation, the proppants that may exist in the sample may be thoroughly distributed from the top to the bottom of the flow-through apparatus 200 after circulation and may be observed. Axial flow driven by the pump 302 may be turned off and/or the bob 208 rotation may be stopped for this observation. The settling of the proppants may be observed visually and/or optically, and associated with the amount of time for the settling to occur. Any development of structure of the proppant particles, including chaining, agglomeration or clumping, may also be observed visually and/or optically. Finally, the sample may be removed and discarded, or saved and considered again after a period of time, from the system 100.

In an embodiment, the disclosed system 100 may be used to conduct friction reduction experiments. Specifically, the system 100 may be used to determine the degradability of a friction reducing agent, by which is implied a component of the fluid and proppant mixture which reduces the required pressure drop and/or power to drive a flow of the mixture. As with embodiments of methods to measure bulk rheological properties, a sample may be deposited into the mixing vessel 300, mixed, heated, pumped, conditioned, fed into the flow-through apparatus 200, and recirculated back to the mixing vessel 300, etc. Bob 208 may be turned on and set at a constant rotational speed. Torque and rotational speed of bob 208 may be continuously monitored. Pressure drop may be measured from the top to the bottom of the mixing vessel 300 and/or the flow-through apparatus 200. After the sample has been sheared and circulated for a set amount of time, bob 208 may be rotated at a set rotational speed. In one embodiment, bob 208 may be set at its maximum rotational speed. The rotational speed of bob 208 may then be decreased linearly over time. Torque acting on the outer surface of bob 208 may be continuously monitored during this decrease. Once the experiment is finished, the sample may be drained from all the components in the system 100 and discarded.

As used herein, the term "particle laden fluids" may refer to any mixture, suspension, solution, or "wellbore servicing fluids" containing particulate matter (e.g., suspended solids). Wellbore servicing fluids are used in a variety of operations and treatments performed in oil and gas wells. Such operations and treatments include without limitation production stimulation operations, such as fracturing, and well completion operations, such as gravel packing.

An example of a production stimulation operation using a wellbore servicing fluid having particles suspended therein is hydraulic fracturing. That is, a type of servicing fluid, referred to as a fracturing fluid, is pumped through a wellbore into a subterranean zone to be stimulated at a rate and pressure such that fractures are formed or enhanced in a desired subterranean zone. It is to be understood that "subterranean formation" encompasses both areas below exposed earth and areas below earth covered by water such as ocean or fresh water. The fracturing fluid is generally a viscoelastic polymeric solution, a gel, emulsion, or foam that may contain a particulate material often referred to as proppant. When used, proppant is deposited in the fracture and functions, inter alia, to hold the fracture open while maintaining conductive channels through which such produced fluids can flow upon completion of the fracturing treatment and release of the attendant hydraulic pressure.

An example of a well completion operation using a servicing fluid having particles suspended therein is gravel packing. Gravel packing treatments are used, inter alia, to reduce the migration of unconsolidated formation particulates into the wellbore. In gravel packing operations, particulates, referred to as gravel, are carried to a wellbore in a subterranean producing zone by a servicing fluid known as carrier fluid. That is, the particulates are suspended in a carrier fluid, which may be viscosified, and the carrier fluid is pumped into a wellbore in which the gravel pack is to be placed. As the particulates are placed in the zone, the carrier fluid leaks off into the subterranean zone and/or is returned to the surface. The resultant gravel pack acts as a filter to separate formation solids from produced fluids while permitting the produced fluids to flow into and through the wellbore. While screenless gravel packing operations are becoming more common, traditional gravel pack operations involve placing a gravel pack screen in the wellbore and packing the surrounding annulus between the screen and the wellbore with gravel designed to prevent the passage of formation particulates through the pack with produced fluids, wherein the wellbore may be oriented from vertical to horizontal and may extend from hundreds to thousands of feed. When installing the gravel pack, the gravel is carried to the formation in the form of a slurry by mixing the gravel with a viscosified carrier fluid. Such gravel packs may be used to stabilize a formation while causing minimal impairment to well productivity. The gravel, inter alia, acts to prevent the particulates from occluding the screen or migrating with the produced fluids, and the screen, inter alia, acts to prevent the gravel from entering the wellbore.

In some situations, the process of hydraulic fracturing and gravel packing are combined into a single treatment to provide a stimulated production and an annular gravel pack to prevent formation sand production. Such treatments are often referred to as "frac pack" operations. In some cases, the treatments are completed with a gravel pack screen assembly in place with the hydraulic fracturing treatment being pumped through the annular space between the casing and the screen. In this situation, the hydraulic fracturing treatment ends in a screen out condition creating an annular gravel pack between the screen and casing. This allows both the hydraulic fracturing treatment and gravel pack to be placed in a single operation. In other cases, the fracturing treatment may be performed prior to installing the screen and placing a gravel pack.

Other examples of wellbore servicing fluids include without limitation spacer fluids, drilling fluids or muds, cementitious fluids (i.e., cement slurries), acidizing fluids, completion fluids, etc. Without limitation, servicing the wellbore includes positioning a sealant composition (e.g., cement) in the wellbore to isolate the subterranean formation from a portion of the wellbore, to support a conduit in the wellbore, to plug a void or crack in the conduit, to plug a void or crack in a cement sheath disposed in an annulus of the wellbore, to plug an opening between the cement sheath and the conduit, to prevent the loss of aqueous or non-aqueous drilling fluids into loss circulation zones such as a void, vugular zone, or fracture, to be used as a fluid in front of cement slurry in cementing operations, to seal an annulus between the wellbore and an expandable pipe or pipe string, or combinations thereof.

Other types of fluids that may be tested using the system 100 and/or the flow-through apparatus 200 include Newtonian and non-Newtonian fluids. To characterize a fluid as one of these, shear stress versus shear rate measurements are made. Shear stress and shear rate measurements may be determined using Couette system assumptions wherein the flow is a steady laminar flow; there is no slip at the surface of the bob 208; the gravity and end effect is negligible thus shearing takes place only angularly ($v_\theta = r\Omega_i$); and both radial and axial velocities are zero ($v_r = v_z = 0$). The shear stress may be calculated as defined in Equation 5, while the shear rate for gaps between $0.5 < \kappa < 0.99$ may be calculated as defined in Equations 6-8 below.

$$T_{r,\theta} = \tau_{r,\theta}(R_i) = \frac{M_i}{2\pi R_i^2 L} \qquad \text{Equation 5}$$

$$\gamma(R_i) = \frac{2\Omega_i}{n(1 - \kappa^{2/n})} \qquad \text{Equation 6}$$

$$\gamma(R_o) = \frac{-2\Omega_i}{n(1 - \kappa^{-2/n})} \qquad \text{Equation 7}$$

$$n = \frac{d \ln M_i}{d \ln \Omega_i} \qquad \text{Equation 8}$$

wherein L is the length of the bob 208 being contacted with sample, $\Omega_i$ is the speed of the bob 208, $R_o$ is the radius of the bob 208 (i.e., the bob casing 209), $R_i$ is the inner radius of the flow chamber 202, and M is the torque acting on the surface of the bob 208.

In Newtonian fluids, the ratio of shear stress to shear rate is a constant at fixed temperature and is called viscosity. Examples of Newtonian fluids are water and certain oils. In non-Newtonian fluids, the shear stress versus shear rate is not constant. Non-Newtonian fluids are classified by their shear stress versus shear rate curves as power law, Bingham, or pseudoplastic fluids. Examples of non-Newtonian fluids include fracture fluid, gels, drilling muds, and cements. In non-Newtonian fluids, certain rheological properties or characteristics, such as viscosity, shear stress, yield stress, consistency, etc. may be measured.

The system 100 may be used to simulate downhole conditions and measure bulk rheological properties such as the shear and temperature history of particle laden fluids. The system 100 may be used to directly measure the rheological properties of particle laden fluids over a wide range of temperatures, pressures, and proppant loading. The system 100 may be used to quantify the shear fields inside the flow-through apparatus 200. The system 100 may be used to determine the dynamic settling of particle laden fluids for example through visual observation. The system 100 may also be used to propose or design the rheological properties of particle laden fluids to service a wellbore. For example, the properties of a particle laden fluid may be adjusted based on the results from the system 100 to better meet the need of a wellbore.

EXAMPLES

The disclosure having been generally described, the following examples are given as particular embodiments of the disclosure and to demonstrate the practice and advantages thereof. It is understood that the examples are given by way of illustration and are not intended to limit the specification or the claims in any manner.

A flow-through apparatus was built according to the following dimensions. The inner radius of the chamber was 36.2 mm. The outer radius of the bob casing was 31.0 mm. The cylindrical bob was 162.56 mm in length. The gap width (d) equals $R_o - R_i = 6.0$ mm. The dimensionless gap ratio ($\delta = d/R_i$)

equals 0.18. The length of the bob being contacted with sample is 161.5 mm. The working height of gap-width is 27.0 mm. The gap ratio of the flow-through apparatus ($\kappa=R_i/R_o$) equals 0.85. A system similar to FIG. 1 was then built using the previously described flow-through apparatus for testing.

Example 1

The effect of the gap width between the inner chamber radius and the outer bob radius on steady state shear rate was evaluated. The experiments were performed using a wide gap Couette system having a gap ratio (defined as the diameter ratio of bob to cup) similar to a flow-through device, and then compared to the experiments performed using a rheometer equipped with standard parallel plate geometry. 7 samples, designated Samples 1-4 and 1A-3A, were prepared. Sample 1 was a base fluid prepared from a mixture of 70 wt. % corn syrup and 30 wt. % glycerol. Samples 2-4 were prepared from base fluids having a solid concentration up to 4 ppg, 6 ppg, and 8 ppg respectively, which are equivalent to a solid volume fraction ($\Phi$) of 0.27, 0.36, and 0.48 respectively. Sample 1A was another base fluid prepared from 0.72 wt. % Xanthan in 12.5 wt. % sodium bromide solution. Samples 2A and 3A were prepared from base fluids having a solid concentration up to 4 ppg and 6 ppg respectively, which are equivalent to a solid volume fraction ($\Phi$) of 0.27 and 0.36 respectively. The solids used in these experiments were neutrally buoyant suspensions of a sphere polymer particle.

Figure 6:
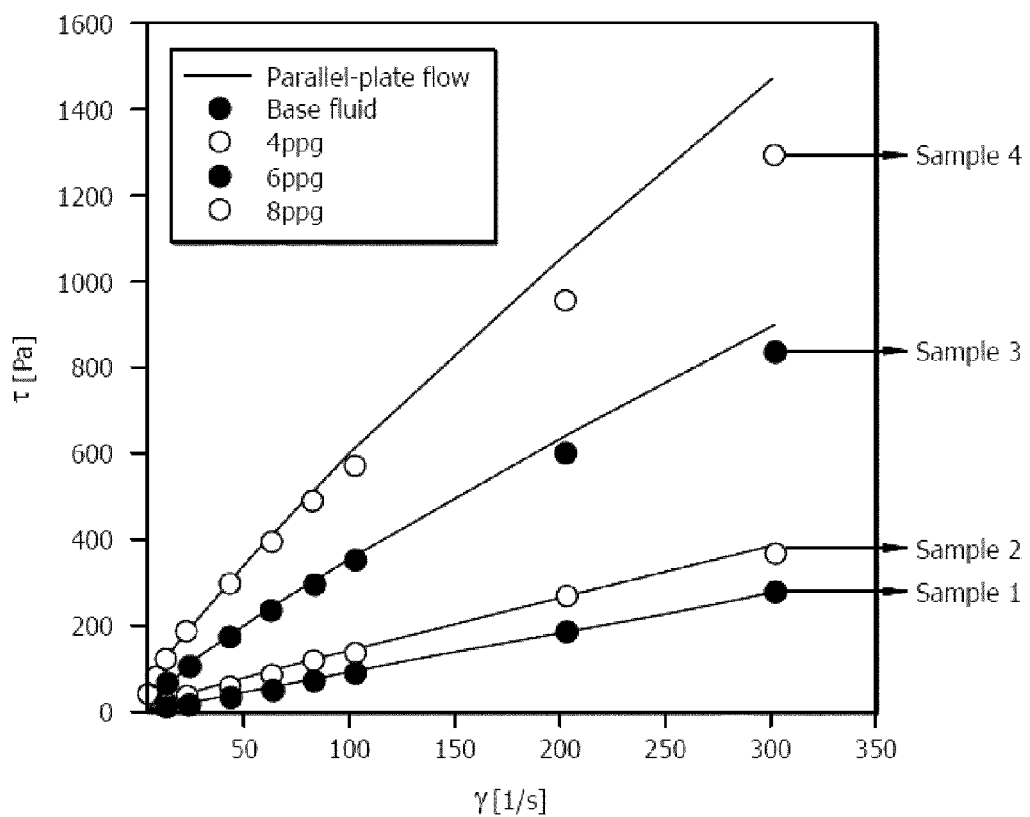
FIG. 6 is a graph of shear stress as a function of shear rate in Newtonian fluid for the samples from Example 1.
Figure 7:
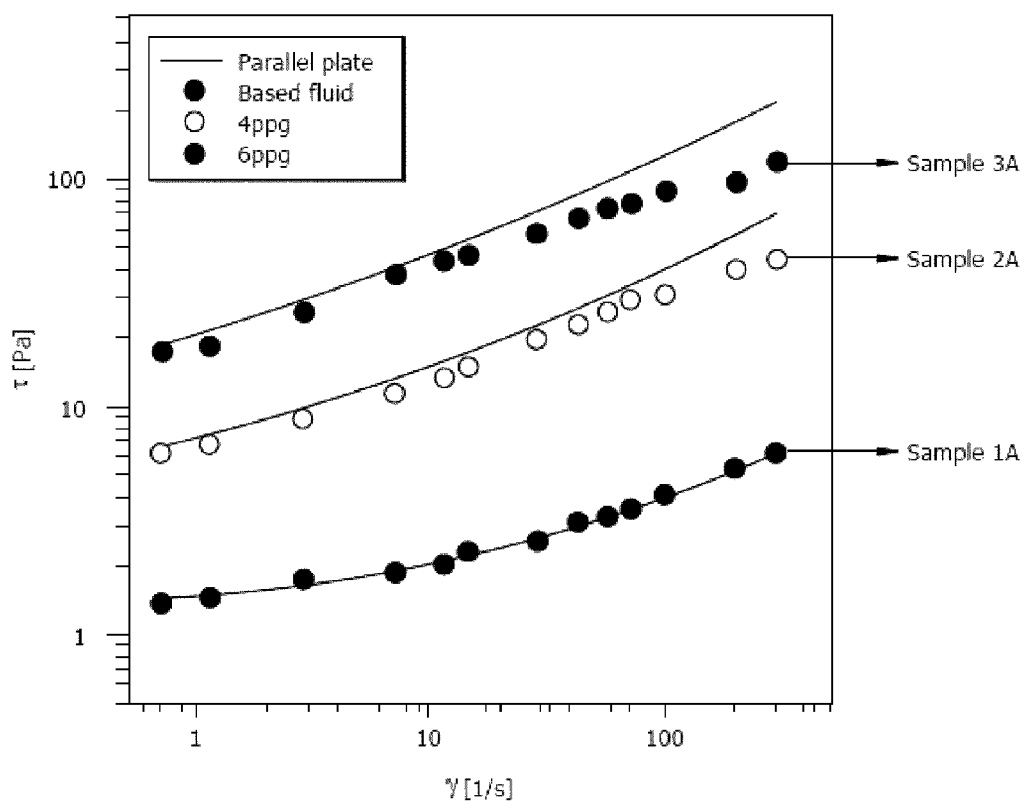
FIG. 7 is a graph of shear stress as a function of shear rate in non-Newtonian fluid for the samples from Example 1.

The experiments were conducted in both Newtonian for Samples 1-4 and non-Newtonian fluid for Samples 1A-3A. FIGS. 6 and 7 are graphs of shear stress as a function of shear rate for Newtonian (Samples 1-4) and non-Newtonian (Samples 1A-3A) fluid respectively. Referring to FIG. 6, Sample 2 showed good agreement between the results from the wide gap Couette system and the parallel plate (i.e., rheometer) throughout the range of shear rates measured. For Samples 3 and 4, good agreements were also observed between the results from the wide gap Couette system and the parallel plate for shear rates up to 100 s$^{-1}$, and small deviations were observed for shear rates above 100 s$^{-1}$. Without wishing to be limited by theory, the small deviations may be due to the shear induced particle migration phenomenon, which is commonly observed for particle laden systems. Examples of such phenomenon in particle laden systems may be found in: J. F. Morris and F. Boulay, *J. Rheol.*, 43, 23 (1999); J. F. Morris and J. F. Brady, *International Journal of Multiphase Flow*, 24, 25, (1997); and J. J. Stickel and R. L. Powell, *Annu. Rev. Fluid Mech.*, 37, 129 (2005), which are incorporated by reference herein in their entirety.

Referring to FIG. 7, good agreements were observed for Samples 1A-3A, especially for shear rates from about 10 s$^{-1}$ to about 40 s$^{-1}$, which are typical shear rates inside fracture paths. Without wishing to be limited by theory, deviations for shear rates above 40 s$^{-1}$ may be due to combinations effects of shear induced particle migration and shear thinning characteristics of the base fluid.

Figure 8:
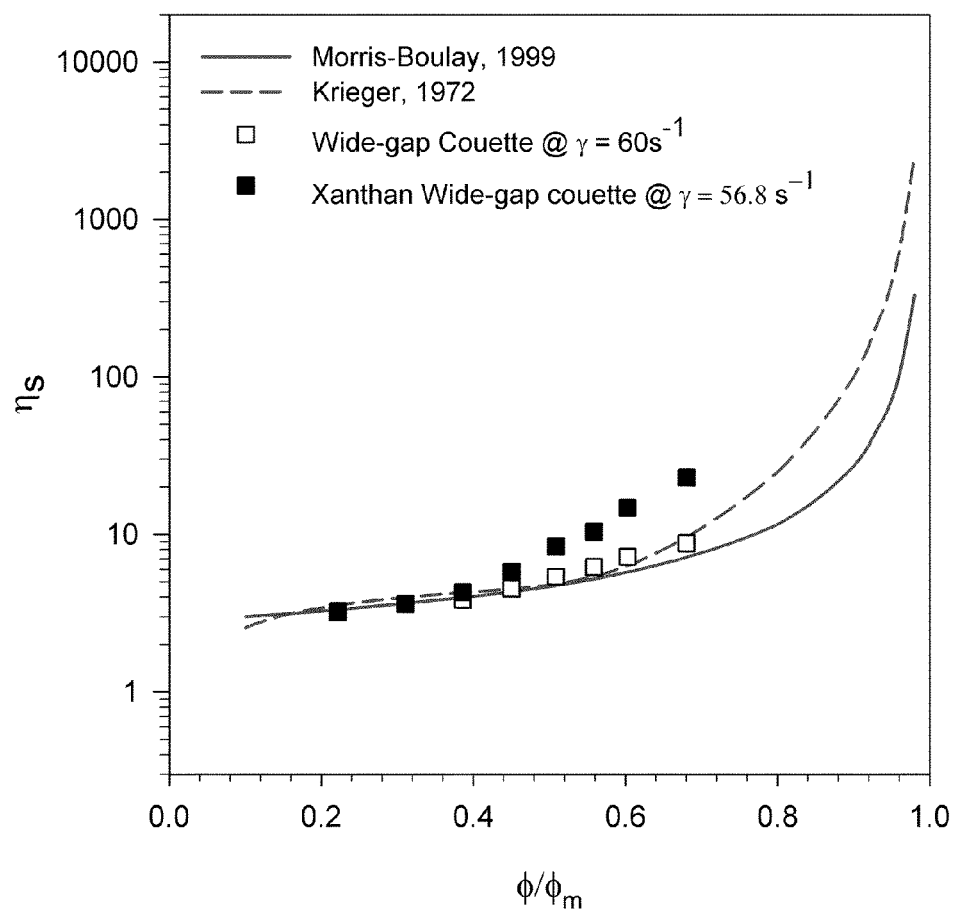
FIG. 8 is a graph of relative viscosity as a function of relative volume fraction for the samples from Example 1.

The method used in shear rate calculation above was also compared to published models for neutrally buoyant particles suspended in a Newtonian base fluid found in J. F. Morris and F. Boulay, *J. Rheol.*, 43, 23 (1999) and I. M. Krieger, *Adv. Colloid Interface Sci.*, 2, 27 (1972), which are incorporated by reference herein in their entirety. FIG. 8 is a graph of relative viscosity as a function of relative volume fraction for the samples from Example 1, Morris-Boulay model, and Krieger model. Referring to FIG. 8, the experimental results for Newtonian (wide-gap Couette system) agreed with the published models, which indicated that the method used herein to calculate shear rate was suitable. However, as expected, the experimental results for non-Newtonian (Xanthan in wide gap Couette) did not agree with the published models as seen by deviations in FIG. 8, which may be due to the effects of shear thinning and yield stress on the distribution of shear rate and stress in the Couette annulus. Additionally, the published models were developed for Newtonian fluids. Such deviations suggested that further improvement is needed on shear rate correction for non-Newtonian. Examples of other techniques to calculate shear rate for non-Newtonian fluids include a two-step technique, which may be found in Q. D. Nguyen and D. V. Boger, *Rheol. Acta*, 26 10 (1987) and Q. D. Nguyen and D. V. Boger, *Annu. Rev. Fluid Mech.*, 24, 42 (1992); a Tiikhonov regularization technique, which may be found in Y. Leong Yeow, W. C. Ko, and P. P. P. Tang, *J. Rheol.*, 44, 17 (2000); and a Wavelet-Vaguellette technique, which may be found in C. Ancey, *J. Rheol.*, 49, 20 (2005), which are incorporated by reference herein in their entirety.

Example 2

Figure 9:
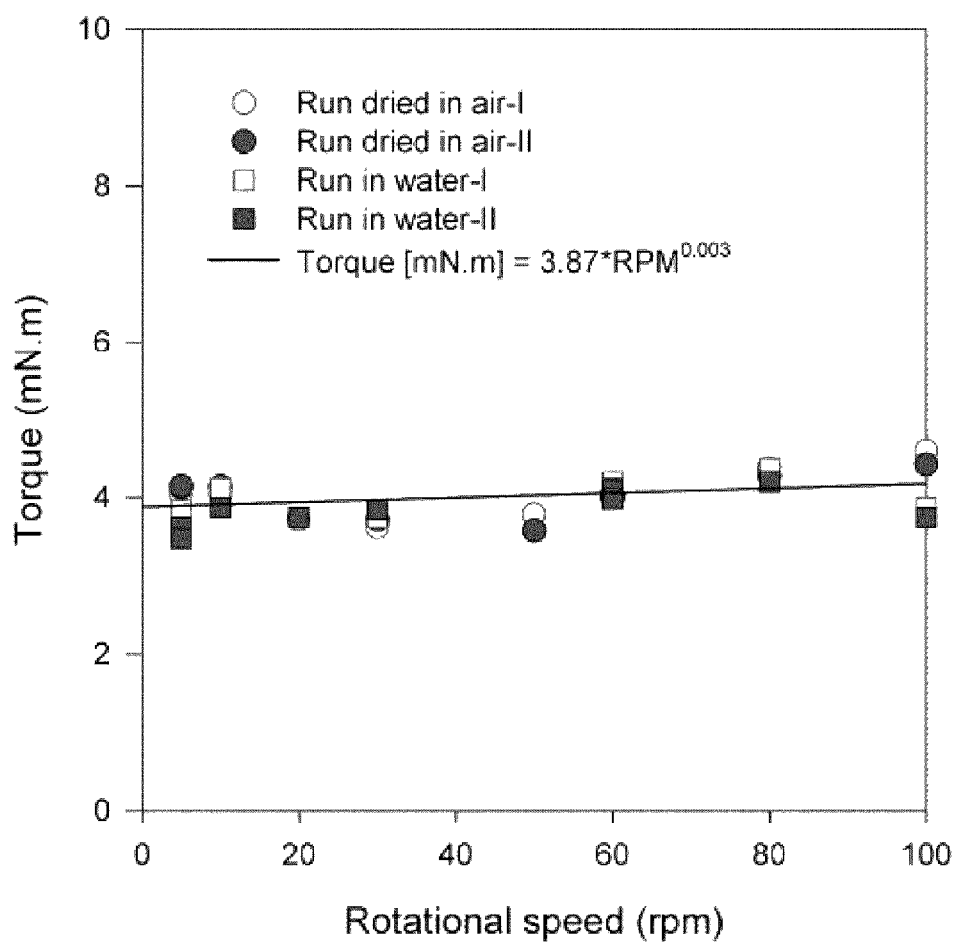
FIG. 9 is a graph of torque as a function of rotational speed for the samples from Example 2.

The effects of inertia (friction drag) on torque sensitivity on a flow-through apparatus were investigated. Four experiments were performed. Experiments 1 and 2 were performed by running air (i.e., dry run) through the flow-through apparatus, while Experiments 3 and 4 were performed by running water through the flow-through apparatus. All experiments were performed at rotational speeds of 5, 10, 20, 30, 50, 60, 80, and 100 rpm. The results are shown in FIG. 9.

The results demonstrated that the effects of inertia that may be dragging the bob during flow measurement were minimized.

Example 3

Figure 10:
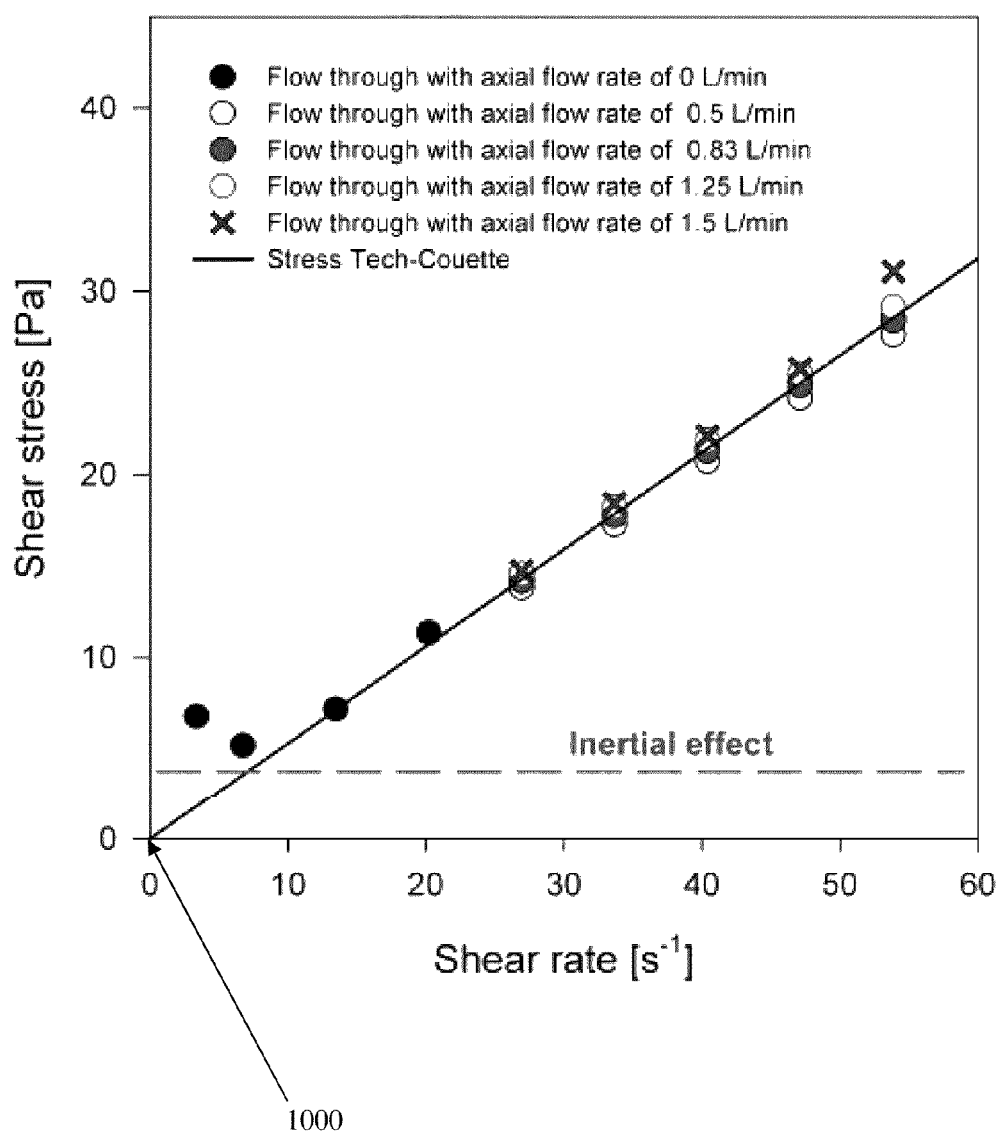
FIG. 10 is a graph of shear stress as a function of shear rate for the samples from Example 3.

The performance of a flow-through apparatus in Newtonian fluid was investigated and compared with the results obtained using a rheometer equipped with a Couette system. Sample 5 was prepared by mixing 70 wt. % corn syrup with 30 wt. % glycerol. The experiments were performed at room temperature and at circulation rates of 0 lpm, 0.5 lpm, 0.83 lpm, 1.25 lpm, and 1.5 lpm and the results are shown in FIG. 10. FIG. 10 is a graph of shear stress as a function of shear rate. Referring to FIG. 10, the relationship between shear stress and shear rate was linear and passed through the origin 1000, indicating the Newtonian characteristics of Sample 5. The results from the flow-through apparatus seemed to agree well with the results from the rheometer, especially at shear rates less than 5 s$^{-1}$. Small deviations were observed between the results from the flow-through apparatus and the rheometer at shear rates greater than 40 s$^{-1}$ for the circulation rate of 1.5 L/min. Without wishing to be limited by theory, the small deviations may be due to the combination effects of axial and radial flows and the effects of air entrance causing instability of the flow inside the flow-through apparatus.

Example 4

Figure 11:
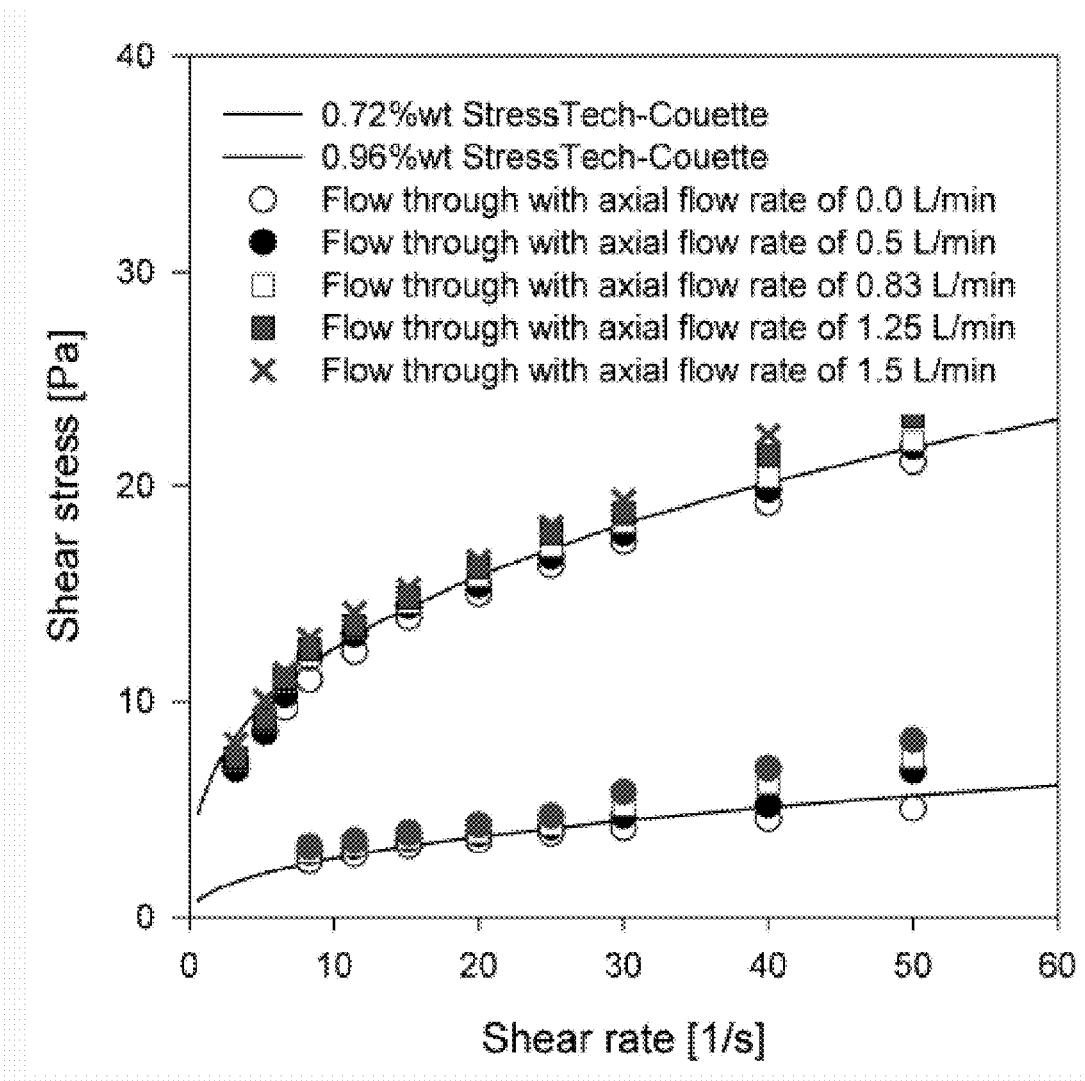
FIG. 11 is a graph of shear stress as a function of shear rate for the samples from Example 4.

The performance of a flow-through apparatus on a sample of a non-Newtonian fluid was investigated and compared with the results obtained using a rheometer equipped with a Couette system. Samples 6 and 7 were prepared by mixing solutions of carboxymethylhydroxypropyl guar (CMHPG) and tap water at 0.72 wt. % and 0.96 wt. % respectively. The experiments were performed at room temperature and at circulation rates of 0 lpm, 0.5 lpm, 0.83 lpm, 1.25 lpm, and 1.5 lpm and the results are shown in FIG. 11. FIG. 11 is a graph of shear stress as a function of shear rate. Referring to FIG. 11, the results indicated that non-Newtonian characteristics were observed as shown by the non-linear relationship between shear stress and shear rate and the results from the flow-through apparatus seemed to agree well with the results from the rheometer. Small deviations were also observed between the results from the flow-through apparatus and the rheometer, which may be due to flow instability and air entrance effects as described previously.

Example 5

The dynamic settling of ceramic proppants in a reversibly crosslinked gel was investigated. The ceramic proppants used in this example were obtained from Carbo Ceramics, Inc., the reversibly crosslinked gel was a mixture of guar powder and water crosslinked with borate ion. The experiment was carried out at an imposed shear rate of 10 s$^{-1}$. An optical laser sheet was used to observe the height of settling of the ceramic proppants inside the flow-through apparatus. The optical laser sheet was set at a gap space between the optical laser sheet and the flow-through apparatus of 1.5 cm, which may be calculated from the angle of the laser probe and its distance from the flow-through apparatus. 15 laser lines were projected onto the flow-through device, which were used as reference lines to measure the height of settling of the ceramic proppants inside the flow-through apparatus. The results are shown in FIG. 12.

Figure 12:
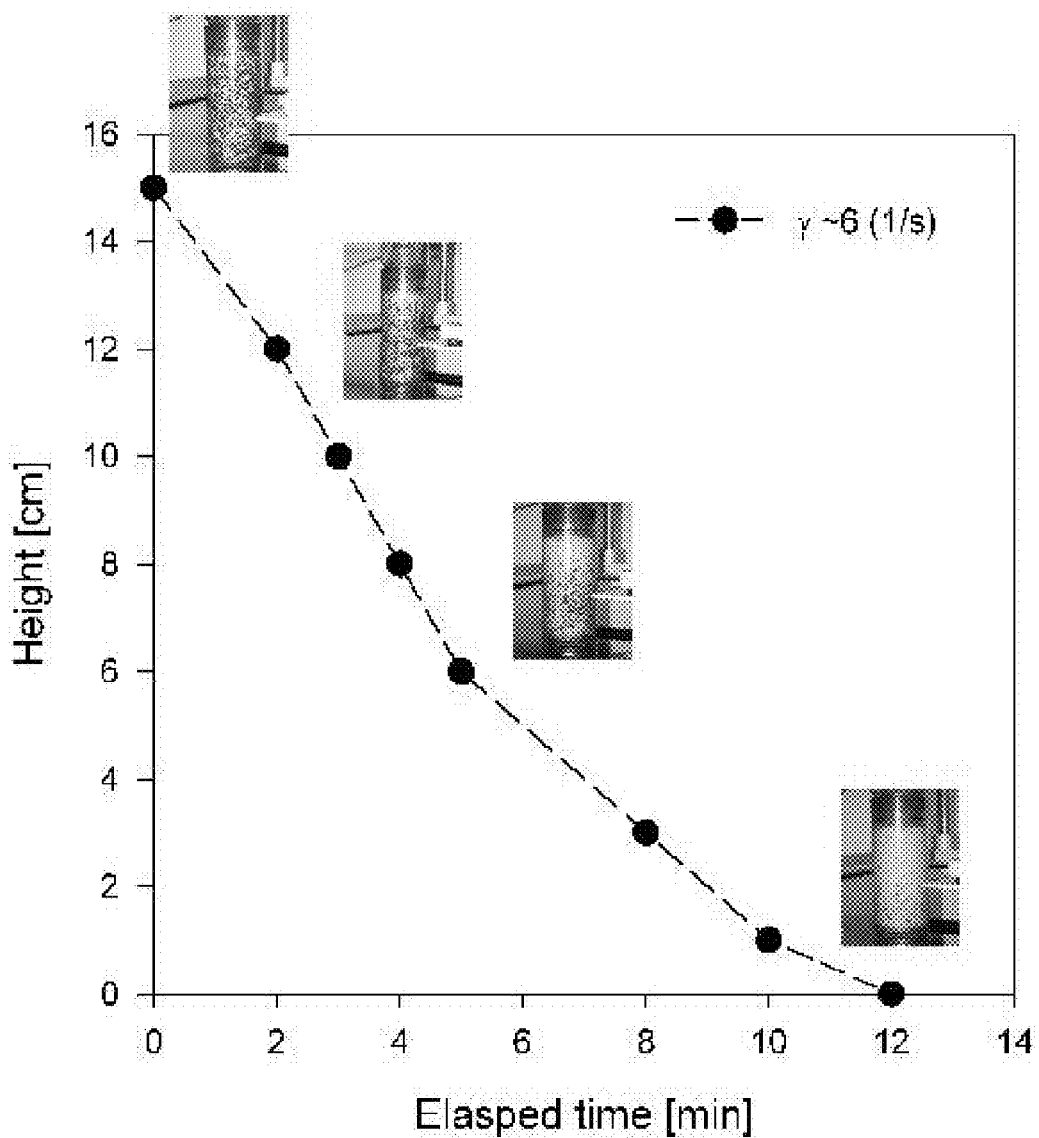
FIG. 12 is a graph of height as a function of elapsed time for the samples from Example 5.

Referring to FIG. 12, the results demonstrated that typical settling phenomenon was observed for this sample using the flow-through apparatus.

Example 6

The static and dynamic settling of ceramic proppants in viscous dominant fluids were investigated. Five samples, designated 8-12 were prepared by mixing guar powder with water to form a mixture. Ceramic proppants with a range of sizes from 0.2 to 1.5 mm were added to the mixture, resulting in a mixture having a solid volume fraction of 0.02. The mixture was reversibly crosslinked by adding borate ion at a borate concentration of 0, 31, 62, 93, and 125 ppm for Samples 8-12 respectively. All samples were uniformly mixed and then fed to the flow-through apparatus. Rheological measurements were carried out by using a Reologica Instruments STRESSTECH controlled-stress rheometer, fitted with a cone-plate fixture. The results are shown in FIGS. 13 and 14.

Figure 13:
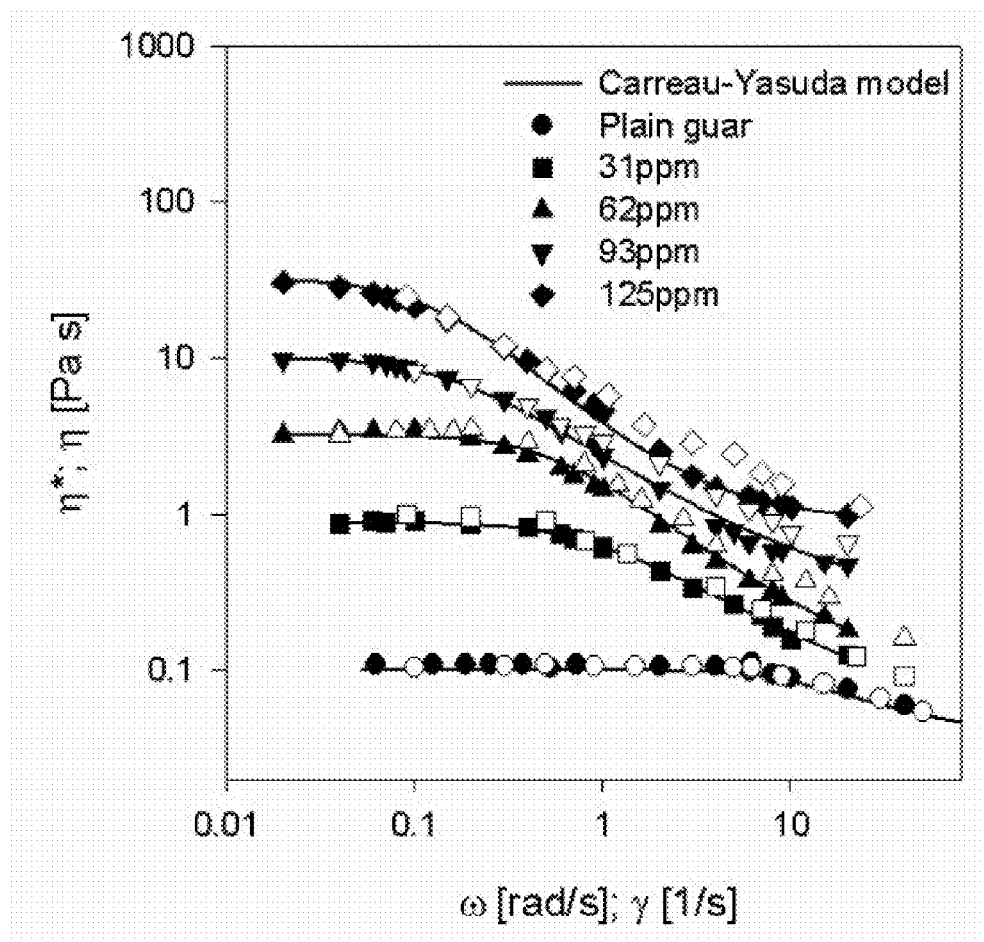
FIG. 13 is a graph of small amplitude oscillatory sweep as a function of shear viscosity for the samples from Example 6.
Figure 14:
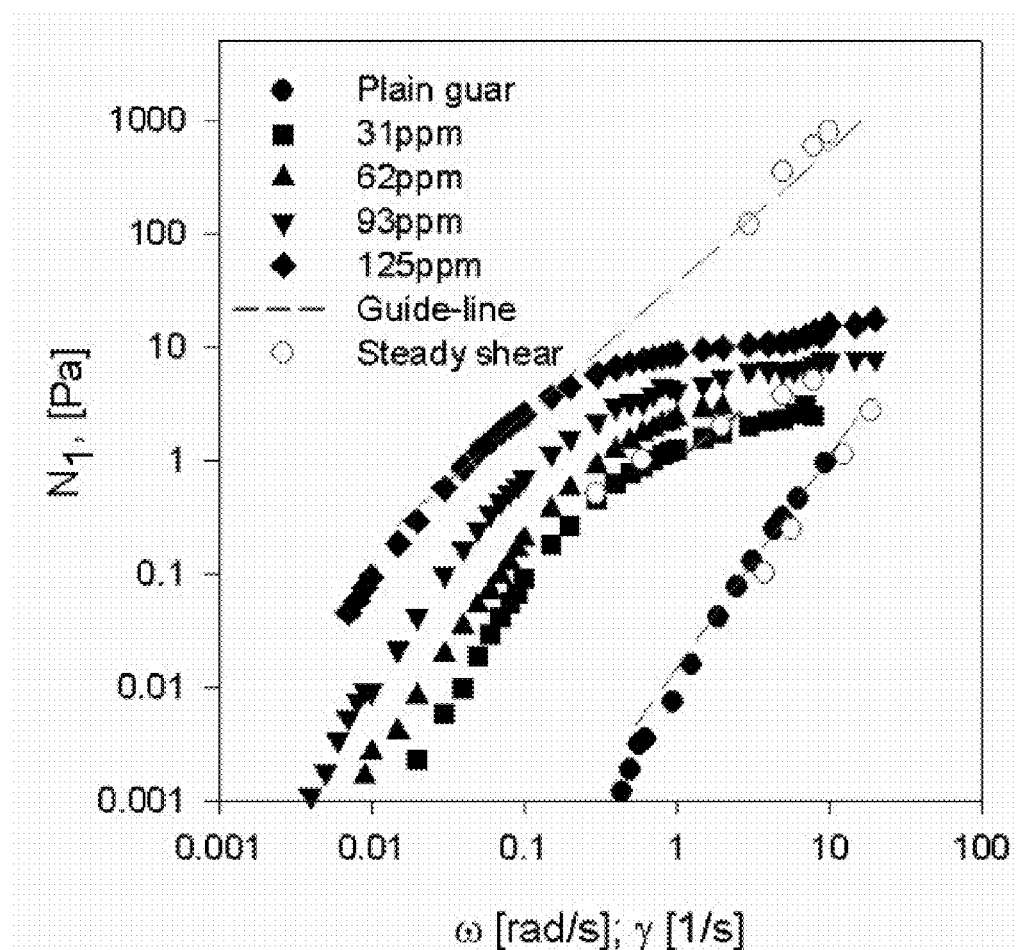
FIG. 14 illustrates the first normal stress difference as a function of shear viscosity for the samples from Example 6.

FIG. 13 illustrates small amplitude oscillatory sweeps (SAOSs) in terms of η*(ω) and η(γ̇) as a function of shear rate ω(γ̇). Herein, the magnitude of η*(ω) is the same as η(γ̇) at equal values of ω and γ̇ for all samples. As shown in FIG. 13, good agreement was observed between the dynamic and steady shear viscosity for Samples 8-10 especially at ω(γ̇) of equal to or greater than 5 s$^{-1}$, while reasonable agreement were observed for Samples 11-12. In addition, the SAOS increases with increasing borate ion concentration as shown in FIG. 13, which implies increased time scale for motion.

The first normal stress coefficient ($\Psi_1$) and the first normal stress difference ($N_1$) were estimated using a Cox-Merz rule shown in Equations 9 and 10 below:

$$\Psi_1 = \frac{2G'}{\omega^2} \quad \text{Equation 9}$$

$$N_1 = \Psi_1 \omega^2 \quad \text{Equation 10}$$

FIG. 14 illustrates the first normal stress difference ($N_1$) as a function of shear viscosity ω(γ̇). Referring to FIG. 14, $N_1$ increases linearly with shear viscosity before approaching steady state at ω of equal to or less than 1 rad/s. Without wishing to be limited by theory, the results suggested that the network structure of the samples had reached their equilibrium state at the given amplitude and frequency. The difference in $N_1$ values obtained from the steady shear and the Cox-Merz value might be due to shear-induced rearrangement of the network junctions from "intra-junction" to "inter-junction". Additionally, the measured $N_1$ is asymptotic with the Cox-Merz data especially at shear rate of equal to or less than 1 s$^-$(rad/s) indicating the practical capability of using the Cox-Merz rule to estimate $N_1$ of the samples.

Figure 15:
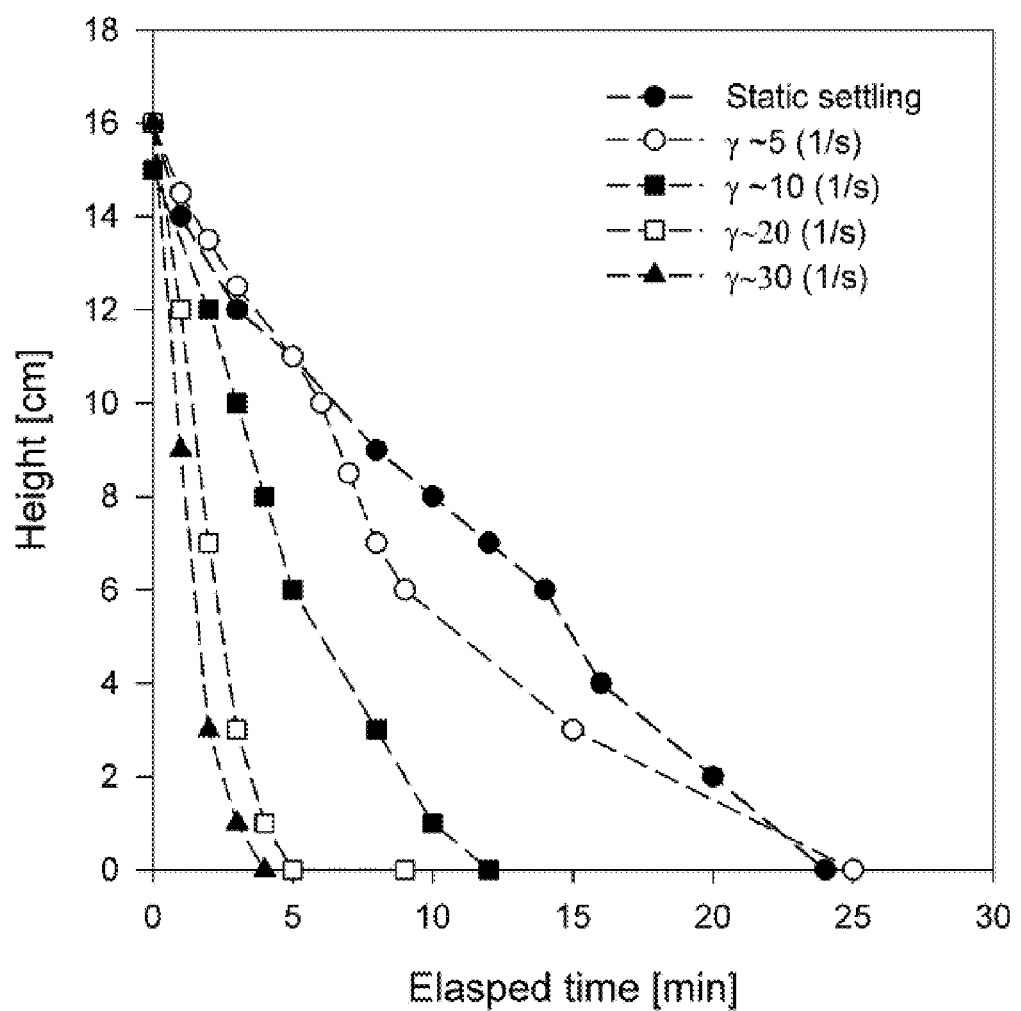
FIG. 15 is a graph of height as a function of elapsed time for the samples from Example 6.
Figure 16:
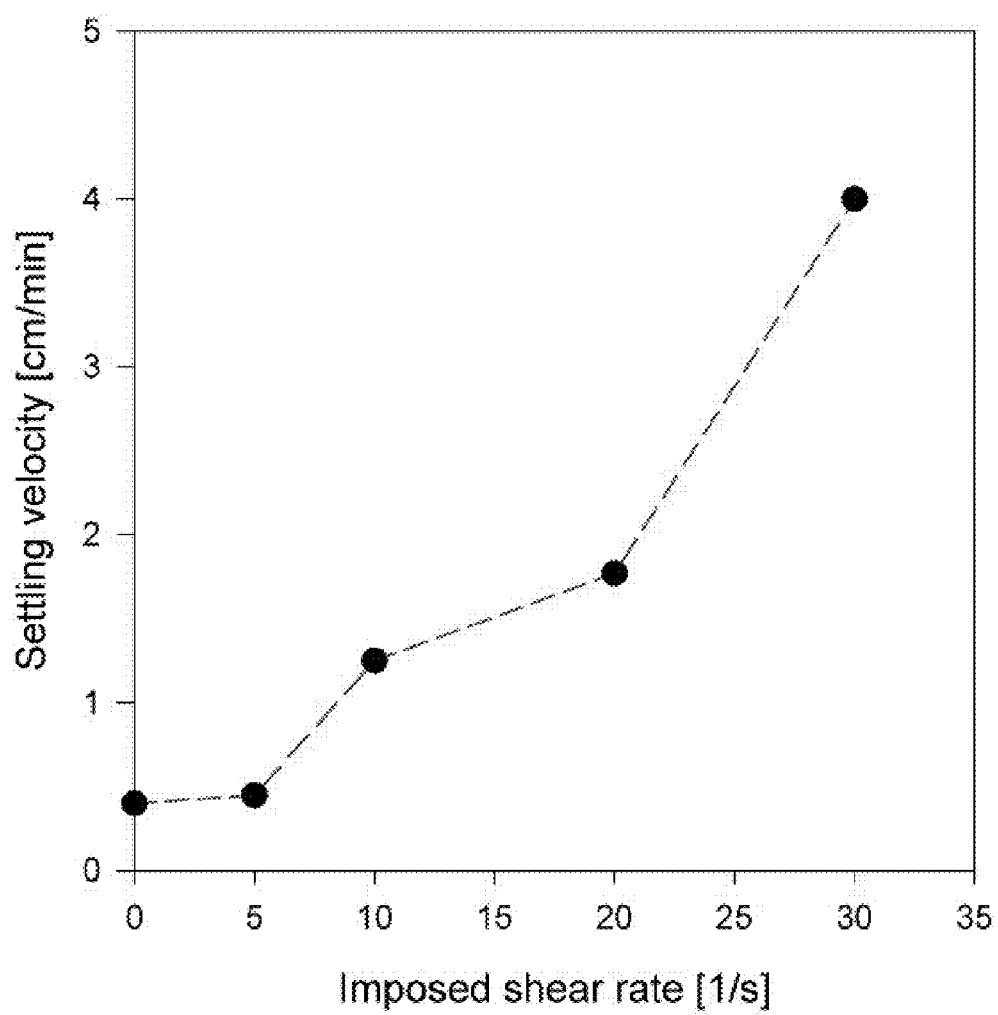
FIG. 16 is a graph of settling viscosity as a function of imposed shear rate for the samples from Example 6.

Sample 10, which is a viscous dominant fluid with a viscous modulus (G") greater than its elastic modulus (G'), was also used to test sedimentation behavior for a wide range of frequency (ω) under five different imposed shear rates of 0 s$^-$(i.e., static settling), 5 s$^{-1}$, 10 s$^{-1}$, 20 s$^{-1}$, and 30 s$^{-1}$. The results are shown in FIGS. 15 and 16. FIG. 15 is a graph of proppant upper surface height as a function of elapsed time. Referring to FIG. 15, the results demonstrated that under static conditions, (i.e., the imposed shear rate was at 0 s$^{-1}$), the particles settled within 25 minutes.

FIG. 16 is a graph of settling viscosity as a function of imposed shear rate. Referring to FIG. 16, the particles settled faster as the settling rate (which is the ratio of the change in settling interface height to the elapsed time) increases with increasing imposed shear rate.

Example 7

Figure 17:
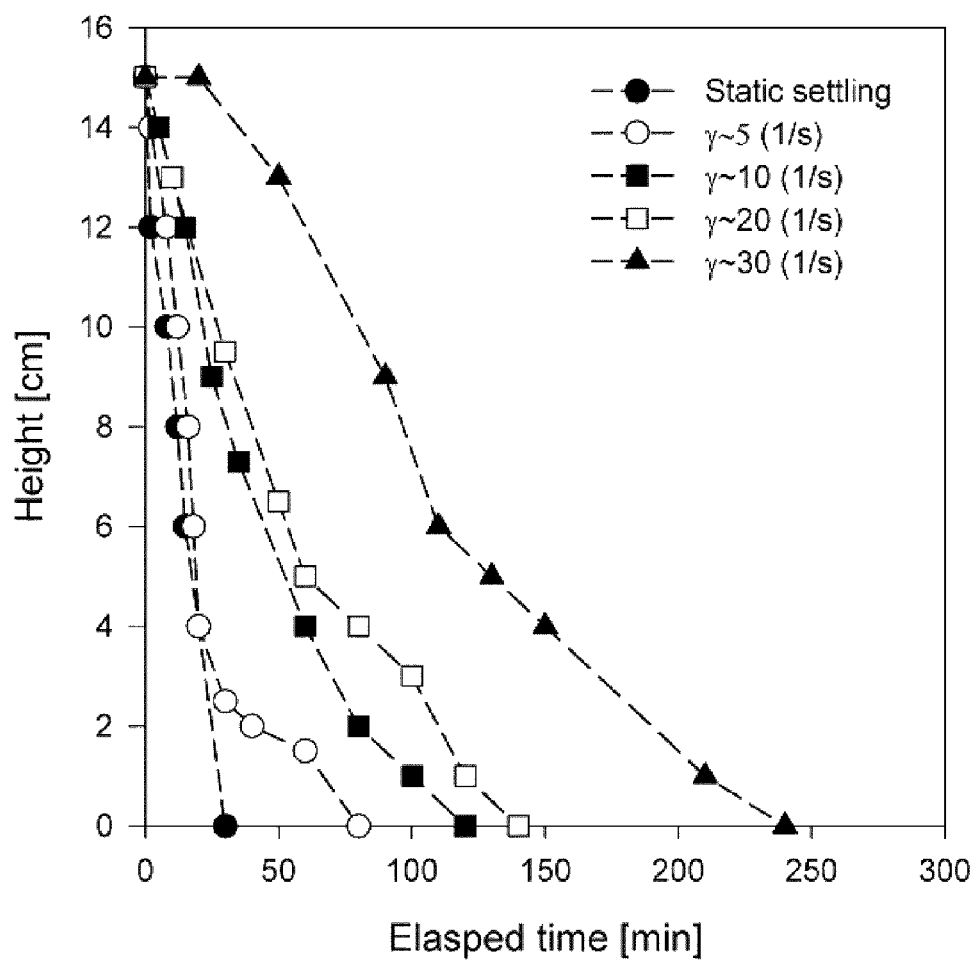
FIG. 17 is a graph of height as a function of elapsed time for the samples from Example 7.

The static and dynamic settling of ceramic proppants in an elastic dominant fluid were investigated. The ceramic proppants used were similar to Example 5. The elastic dominant fluid used was 0.003 g/ml of carboxymethylhydroxypropyl guar (CMHPG), which has a viscous modulus (G") lower than its elastic modulus (G') for a wide range of frequency (ω) under five different imposed shear rates of 0 s$^{-1}$ (i.e., static settling), 5 s$^{-1}$, 10 s$^{-1}$, 20 s$^{-1}$, and 30 s$^{-1}$. The results are shown in FIG. 17. The results demonstrated that the ceramic proppants settled slower as the imposed shear rate increased. The ceramic proppants were found to settle within 250 minutes for the shear rate of 30 s$^{-1}$.

Figure 18:
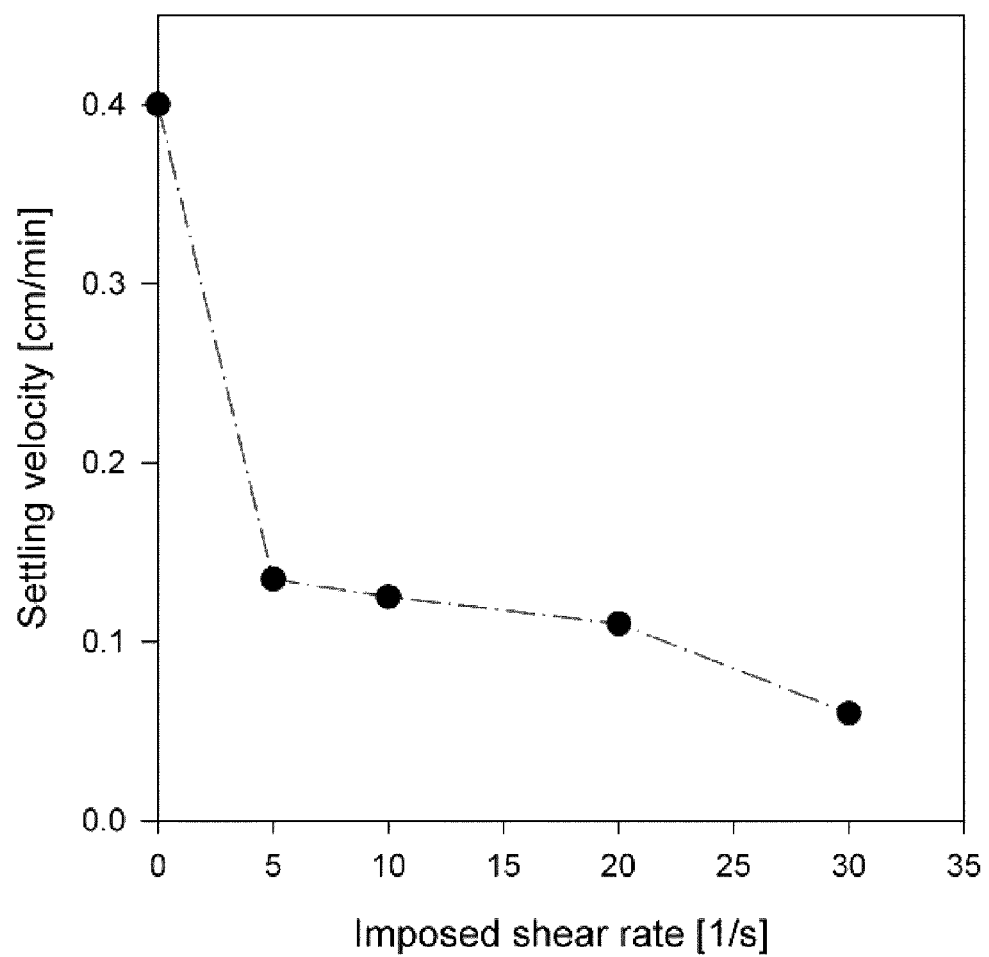
FIG. 18 is a graph of settling viscosity as a function of imposed shear rate for the samples from Example 7.

FIG. 18 is a graph of settling viscosity as a function of imposed shear rate for the samples from Example 7. Without wishing to be limited by theory, the settling behavior in an elastic dominant fluid was contrary to the settling behavior in a viscous dominant fluid in Example 6.

While embodiments of the disclosure have been shown and described, modifications thereof can be made by one skilled in the art without departing from the spirit and teachings of the disclosure. The embodiments described herein are exemplary only, and are not intended to be limiting. Many variations and modifications of the disclosure disclosed herein are possible and are within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_L$, and an upper limit, $R_U$, is disclosed, any number falling within the range is specifically disclosed. In particular, the following numbers within the range are specifically disclosed: $R=R_L+k*(R_U-R_L)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the embodiments of the present disclosure. The discussion of a reference in the Description of Related Art is not an admission that it is prior art to the present disclosure, especially any reference that may have a publication date after the priority date of this application. The disclosures of all patents, patent applications, and publications cited herein are hereby incorporated by reference, to the extent that they provide exemplary, procedural, or other details supplementary to those set forth herein.

What is claimed is:

1. A method of determining one or more bulk rheological properties of a particle laden fluid comprising:
    (a) providing a system comprising a vessel that comprises at least one of a mixer and an agitator, a pump coupled to the vessel, and a flow-through apparatus coupled to the pump and the vessel, wherein
    the flow-through apparatus comprises a flow chamber, a bob rotatably disposed within the chamber, wherein the bob comprises an outer geometry adapted for continuous laminar flow in an axial direction, and a gap between the chamber and the bob;
    (b) pumping the particle laden fluid into the flow-through apparatus;
    (c) shearing the particle laden fluid within the gap of the flow-through apparatus;
    (d) developing a laminar flow of the particle laden fluid through the flow-through apparatus in the axial direction while shearing the particle laden fluid within the gap; and
    (e) collecting data from the bob and observing the particle laden fluid to determine one or more bulk rheological properties of the particle laden fluid.

2. The method of claim 1 wherein (c) comprises shearing the fluid within the gap as the bob rotates and the fluid continuously flows through the flow chamber of the flow-through apparatus.

3. The method of claim 1 wherein (c) comprises shearing the fluid within the gap as the bob remains stationary and the fluid continuously flows through the flow chamber.

4. The method of claim 1 wherein (c) comprises shearing the fluid within the gap by rotating the bob while the fluid remains stationary within flow chamber.

5. The method of claim 1 wherein the particle laden fluid is observed within the gap as the bob and the fluid remains stationary within flow chamber.

6. The method of claim 1 wherein one or more bulk rheological properties comprises shear stress, viscosity, fluid velocity, or combinations thereof.

7. The method of claim 1, further Comprising heating the particle laden fluid within the vessel.

8. The method of claim 1, further comprising measuring the pressure from the top to the bottom of the vessel, from the top to the bottom of the flow-through apparatus, or combinations thereof.

9. The method of claim 1, further comprising measuring the temperature of the fluid at one or more locations within the system.

10. The method of claim 9 wherein the one or more locations comprises inside the vessel, inside the sample conditioning unit, inside the flow-through apparatus, or combinations thereof.

11. The method of claim 1, further comprising changing the rotational speed of the bob and repeating (c) and (d).

12. The method of claim 1, further comprising changing the size of the bob.

13. The method of claim 1, further comprising changing the speed of the pump.

14. The method of claim 1 wherein the flow chamber further comprises a view portion.

15. The method of claim 14, further comprising visually or optically observing the particle laden fluid within the flow-through device through the view portion.

16. The method of claim 1, further comprising pre-conditioning the particle laden fluid before (b) to simulate downhole conditions.

17. The method of claim 1 wherein the particle laden fluid is a fracturing fluid.

18. The method of claim 1 wherein the particle laden fluid is a fluid to be used in a wellbore servicing.

19. A system for testing a particle laden fluid comprising:
    a mixing vessel;
    a conditioning unit coupled to said mixing vessel for pre-conditioning the shear and the temperature of the particle laden fluid;
    a flow-through apparatus coupled to said conditioning unit and said mixing vessel, wherein said flow-through apparatus comprises a flow chamber having a view portion;
    a bob rotatably disposed within said flow chamber, wherein said bob comprises an outer geometry adapted for continuous laminar flow in an axial direction, and wherein said view portion allows for optical and visual measurement of the particle laden fluid as said bob rotates and the particle laden fluid flows through said flow chamber; and
    one or more inlet and one or more outlet in fluid communication with said flow chamber, said inlet and said outlet allow for said continuous laminar flow of the particle laden fluid in said axial direction across said entire outer geometry of said bob through said flow-through apparatus.

20. An apparatus for testing a particle laden system comprising:
    a flow chamber, wherein said flow chamber has a view portion;
    a bob rotatably disposed within said flow chamber, wherein said bob comprises an outer geometry adapted for continuous laminar flow in an axial direction, wherein a first end and a second end of said bob comprises a frusto-conical surface, and wherein said view portion allows for optical measurement and visual observation of the particle laden system as said bob rotates, and
    at least one inlet and at least one outlet in fluid communication with said flow chamber, said inlet and said outlet allow for said continuous laminar flow of a particle laden fluid in said axial direction across said entire outer geometry of said bob through said flow chamber while said bob is rotating.

* * * * *